(12) United States Patent
Lizardi et al.

(10) Patent No.: US 6,403,319 B1
(45) Date of Patent: Jun. 11, 2002

(54) ANALYSIS OF SEQUENCE TAGS WITH HAIRPIN PRIMERS

(75) Inventors: Paul M. Lizardi, Wallingford; Darin R. Latimer, East Haven, both of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/637,384

(22) Filed: Aug. 11, 2000

Related U.S. Application Data

(63) Continuation-in-part of application No. 09/544,713, filed on Apr. 6, 2000, now Pat. No. 6,261,782.
(60) Provisional application No. 60/148,870, filed on Aug. 13, 1999.

(51) Int. Cl.[7] .......................... C12Q 1/68; C12P 19/34; C07H 21/04
(52) U.S. Cl. ....................... 435/6; 435/91.2; 536/24.3
(58) Field of Search .................. 435/6, 91.2, 810; 536/24.3

(56) References Cited

U.S. PATENT DOCUMENTS

| | | | |
|---|---|---|---|
| 4,883,750 A | | 11/1989 | Whiteley et al. |
| 5,215,899 A | * | 6/1993 | Dattagupta ............... 435/6 |
| 5,354,668 A | | 10/1994 | Auerbach |
| 5,429,807 A | | 7/1995 | Matson et al. |
| 5,455,166 A | | 10/1995 | Walker |
| 5,503,980 A | | 4/1996 | Cantor |
| 5,508,169 A | | 4/1996 | Deugau et al. |
| 5,521,065 A | | 5/1996 | Whiteley et al. |
| 5,591,609 A | | 1/1997 | Auerbach |
| 5,599,695 A | | 2/1997 | Pease et al. |
| 5,614,389 A | | 3/1997 | Auerbach |
| 5,654,413 A | * | 8/1997 | Brenner .................. 536/22.1 |
| 5,733,733 A | | 3/1998 | Auerbach |
| 5,798,210 A | * | 8/1998 | Canard et al. ............ 435/6 |
| 5,854,033 A | | 12/1998 | Lizardi |
| 5,854,413 A | | 12/1998 | Hawkins et al. |
| 5,858,656 A | | 1/1999 | Deugau et al. |
| 5,866,336 A | * | 2/1999 | Nazarenko et al. ........ 435/6 |
| 5,871,928 A | | 2/1999 | Fodor et al. |
| 5,962,221 A | * | 10/1999 | Caetano-Anolles ........ 435/6 |
| 6,007,987 A | | 12/1999 | Cantor et al. |
| 6,037,130 A | * | 3/2000 | Tyagi et al. ............. 435/6 |
| 6,074,818 A | * | 6/2000 | Caetano-Anolles et al. ... 435/6 |

FOREIGN PATENT DOCUMENTS

WO    WO 97/19193    5/1997

OTHER PUBLICATIONS

Adams, et al., "Complementary DNA sequencing: expressed sequence tags and human genome project," *Science* 252(5013):1651–56 (1991).

(List continued on next page.)

*Primary Examiner*—Kenneth R. Horlick
(74) *Attorney, Agent, or Firm*—Needle & Rosenberg, P.C.

(57) ABSTRACT

Disclosed is a method for the comprehensive analysis of nucleic acid samples and a detector composition for use in the method. The method involves amplifying nucleic acid fragments of interest using a primer that can form a hairpin structure; sequence-based coupling of the amplified fragments to detector probes; and detection of the coupled fragments. The amplified fragments are coupled by hybridization and coupling, preferably by ligation, to detector probes. A hairpin structure formed at the end of the amplified fragments facilitates coupling of the fragments to the probes. The method allows detection of the fragments where detection provides some sequence information for the fragments. The method allows a complex sample of nucleic acid to be quickly and easily cataloged in a reproducible and sequence-specific manner. The method can also be used to detect amplified fragments having a known sequence.

106 Claims, 7 Drawing Sheets

OTHER PUBLICATIONS

Adams, et al., "Initial assessment of human gene diversity and expression patterns based upon 83 million nucleotides of cDNA sequence," *Nature* 377:3–174 (1995).

Alwine, et al., "Method for detection of specific RNAs in agarose gels by transfer to diazobenzyloxymethyl–paper and hybridization with DNA probes," *Proc. Natl. Acad. Sci. U. S. A.* 74(12):5350–4 (1977).

Bauer, et al., "Identification of differentially expressed mRNA species by an improved display technique (DDRT-PCR)," *Nucleic Acids Res.* 21(18):4272–80 (1993).

Birkenmeyer & Mushahwar, "DNA probe amplification methods," *J. Virol. Methods* 35(2):117–26 (1991).

Breslauer, et al., "Predicting DNA duplex stability from the base sequence," *Proc. Natl. Acad. Sci. U. S. A.* 83(11):3746–50 (1986).

Chee, et al., "Accessing genetic information with high–density DNA arrays," *Science* 274(5287):610–4 (1996).

Diatchenko, et al, "Suppression subtractive hybridization: a method for generating differentially regulated or tissue–specific cDNA probes and libraries," *Proc. Natl. Acad. Sci. U. S. A.* 93(12):6025–30 (1996).

Edman, et al., "Identification of ErbB3–stimulated genes using modified representational difference analysis," *Biochem. J.* 323 ( Pt 1):113–8 (1997).

Fodor, et al., "Multiplexed biochemical assays with biological chips," *Nature* 364:555–556 (1993).

Freier, et al., "Improved free–energy parameters for predictions of RNA duplex stability," *Proc. Natl. Acad. Sci. U. S. A.* 83(24):9373–7 (1986).

Guo, et al., "Direct fluorescence analysis of genetic polymorphisms by hybridization with oligonucleotide arrays on glass supports," *Nucleic Acids Res.* 22(24):5456–5465 (1994).

Hedrick, et al., "Isolation of cDNA clones encoding T cell–specific membrane–associated proteins," *Nature.* 308(5955):149–53 (1984).

Hermanson, et al., eds., *Immobilized Affinity Ligands.* (Academic Press, New York, 1992).

Hoheisel, "Sequence–independent and linear variation of oligonucleotide DNA binding stabilities," *Nucleic Acids Res.* 24(3):430–2 (1996).

Horn, et al., "An improved divergent synthesis of comb-type branched oligodeoxyribonucleotides (bDNA) containing multiple secondary sequences," *Nucleic Acids Res.* 25(23):4835–41 (1997).

Hoy, et al., "Bromodeoxyuridine/DNA analysis of replication in CHO cells after exposure to UV light," *Mutat. Res.* 290(2):217–30 (1993).

Hubank & Schatz, "Identifying differences in mRNA expression by representational difference analysis of cDNA," *Nucleic Acids Res.* 22(25):5640–8 (1994).

Ito & Sakaki, "Fluorescent differential display," *Methods Mol. Biol.* 85:37–44 (1997).

Johnstone & Thorpe, *Immunochemistry In Practice* (Blackwell Scientific Publications, Oxford, England, 1987) pp. 209–216 and 241–242.

Kerkhof, "A Comparison of Substrates for Quantifying the Signal from a Nonradiolabeled DNA Probe," *Analytical Biochemistry* 205:359–364 (1992).

Khrapko, et al., "Hybridization of DNA with oligonucleotides immobilized in a gel: a convenient method for recording single base replacements," *Mol. Biol. (Mosk).* 25(3):718–30 (1991).

Landegren, "Molecular mechanics of nucleic acid sequence amplification," *Trends Genetics* 9:199–202 (1993).

Langer, et al., "Enzymatic synthesis of biotin–labeled polynucleotides: Novel nucleic acid affinity probes", *Proc. Natl. Acad. Sci. USA* 78(11):6633–6637 (1981).

Lavery, et al., "Selective amplification via biotin– and restriction–mediated enrichment (SABRE), a novel selective amplification procedure for detection of differentially expressed mRNAs," *Proc. Natl. Acad. Sci. U. S. A.* 94(13):6831–6 (1997).

Lee, et al., "Comparative expressed–sequence–tag analysis of differential gene expression profiles in PC–12 cells before and after nerve growth factor treatment," *Proc. Natl. Acad. Sci. U. S. A.* 92(18):8303–7 (1995).

Liang & Pardee, "Differential display of eukaryotic messenger RNA by means of the polymerase chain reaction," *Science,* 57(5072):967–71 (1992).

Liang & Pardee, "Recent advances in differential display," *Curr. Opin. Immunol.* 7(2):274–80 (1995).

Lisitsyn, et al., "Cloning the differences between two complex genomes," *Science* 259(5097):946–51 (1993).

Lizardi, et al., "Mutation detection and single–molecule counting using isothermal rolling–circle amplification," *Nat Genet.* 19(3):225–32 (1998).

Maniatis, et al., "The isolation of structural genes from libraries of eucaryotic DNA," *Cell* 15(2):687–701 (1978).

Nguyen, et al., "Modification of DNA duplexes to smooth their thermal stability independently of their base content for DNA sequencing by hybridization," *Nucleic Acids Res.* 25(15):3059–3065 (1997).

Nguyen, et al., "Smoothing of the thermal stability of DNA duplexes by using modified nucleosides and chaotropic agents," *Nucleic Acids Res.* 27(6):1492–1498 (1999).

O'Neill & Sinclair, "Isolation of rare transcripts by representational difference analysis," *Nucleic Acids Res.* 25:2681–2682 (1997).

Pease, et al., "Light–generated oligonucleotide arrays for rapid DNA sequence analysis," *Proc. Natl. Acad. Sci. USA* 91(11):5022–5026 (1994).

Prashar & Weissman, "Analysis of differential gene expression by display of 3' end restriction fragments of cDNAs," *Proc. Natl. Acad. Sci U.S.A.* 93:659–663 (1996).

Santa Lucia, et al., "Improved nearest–neighbor parameters for predicting DNA duplex stability," *Biochemistry* 35:3555–3562 (1996).

Schena, et al., "Quantitative Monitoring of Gene Expression Patterns with a Complementary DNA Microarray," *Science* 270:467–470 (1995).

Stimpson, et al., "Real–time detection of DNA hybridization and melting on oligonucleotide arrays by using optical wave guides," *Proc. Natl. Acad. Sci. USA* 92(14):6379–6383 (1995).

Swaroop, et al., "A simple and efficient cDNA library subtraction procedure: isolation of human retina–specific cDNA clones," *Nucleic Acids Res.* 19(8):1954 (1991).

Syvänen, et al., "Fast quantification of nucleic acid hybrids by affinity–based hybrid collection," *Nucleic Acids Res.* 14(12):5037–48 (1986).

Taylor, *Protein immobilization: fundamentals and applications* (M. Dekker, New York, 1991).

Urdea, "Branched DNA signal amplification," *Biotechnology (N Y)*. 12(9):926–8 (1994).

Vasmatzis, et al., "Discovery of three genes specifically expressed in human prostate by expressed sequence tag database analysis," *Proc. Natl. Acad. Sci. U. S. A.* 95:300–304 (1998).

Velculescu, et al., "Serial analysis of gene expression," *Science*. 270(5235):484–7 (1995).

Wada, et al., "Representational difference analysis of cDNA of genes expressed in embryonic kidney," *Kidney Int.* 51:1629–1638 (1997).

Wansink, et al., "Fluorescent Labeling of Nascent RNA Reveals Transcription by RNA Polymerase II in Domains Scattered Throughout the Nucleus," *Journal of Cell Biology* 122(2): 283–293 (1993).

Wood, et al., "Base composition–independent hybridization in tetramethylammonium chloride: a method for oligonucleotide screening of highly complex gene libraries," *Proc. Natl. Acad. Sci.* USA 82(6):1585–1588 (1985).

Yu, et al., "Cyanine dye dUTP analogs for enzymatic labeling of DNA probes," *Nucleic Acids Research* 22(15):3226–3232 (1994).

* cited by examiner-

Figure 1A

Hairpin primer 1

5'-HHHHHHHHHHnnnnnnnnnnnnnnnnnnppppppppppPPPPPPPPPP-3'

```
                                        nnnnnnnnnnnnn
                         HHHHHHHHHH                  n
      ...ffffffffffffffffffffffffPPPPPPPPPP          n
                                        ppppppppppnnn
```

Hairpin primer 2

5'-HHHHHHHHHHnnnnnnnnnnnnnnnnnnnnnnppppppPPPPPPPPPPpppp-3'

```
                                           nnnnnnnnnnnnn
                            HHHHHHHHHH                  n
         ...ffffffffffffffffffffffffffppppPPPPPPPPPP    n
                                           ppppppnnnnnnn
```

Hairpin primer 3

5'-HHHHHHHHHHnnnnnnnnnnnnnnnnnnnnnnppppppppppppppPPPPPP-3'

```
                                           nnnnnnnnnnnnnnnnn
                            HHHHHHHHHH                       n
         ...ffffffffffffffffffffffFFFFPPPPPP                 n
                                           ppppppppppppppnnn
```

Hairpin primer 4

5'-HHHHHHHHHHnnnnnnnnnnppppppppppPPPPPPPPPP-3'

```
                                         nnnnnnnnn
                          HHHHHHHHHH              n
       ...ffffffffffffffffffffffffPPPPPPPPPP      p
                                         ppppppppp
```

Hairpin primer 5

5'-HHHHHHHHHHnnppppppppppPPPPPPPPPP-3'

```
                                         nnppp
                          HHHHHHHHHH          p
       ...ffffffffffffffffffffffffPPPPPPPPPP  p
                                         ppppp
```

Figure 1B

Hairpin primer 6

```
5'-HHHHHHHHHHHHnnnnnnnnnnnnnnnnppppppppPPPPPPPPPPPP-3'
                                          nnnnnnnnnnn
                              HHHHHHHHHHHH           n
       ...ffffffffffffffffffffffffPPPPPPPPPPPP       n
                                          ppppppppnnn
```

Hairpin primer 7

```
5'-HHHHHHHHnnnnnnnnnnnnnnnnnppppppppppppPPPPPPPP-3'
                                          nnnnnnnnnnnn
                                  HHHHHHHH            n
       ...ffffffffffffffffffffffffPPPPPPPP            n
                                          ppppppppppppn
```

Hairpin primer 8

```
5'-HHHnnnnnnnnnnnnnnnnnnnnnnppppppppppppppppppPPP-3'
                                          nnnnnnnnnnnnnnnnn
                                       HHH                  n
       ...ffffffffffffffffffffffffPPP                       n
                                          ppppppppppppppppppn
```

Hairpin primer 9

```
5'-HHHHHHHHHHHHHHHHHHnnnnnnPPPPPPPPPPPPPP-3'
                                          nn
                              HHHHHHHHHHHHHHHH   n
       ...ffffffffffffffffffffffffPPPPPPPPPPPPPP n
                                          nn
```

Hairpin primer 10

```
5'-HHHHHHHHHHnnnnnnnnnnnnnnnnppppppppppPPPPPPPPPP-3'
                                          nnnnnnnnnnn
                                HHHHHHHHHH           n
       ...ffffffffCCTACffffffffPPPPPPPPPP            n
                                          ppppppppppnnn
```

Figure 4

Amplified fragment

```
3'-...CTCATACGACTCACATTCAGCGAACTCGACGGCCTAAGTTCGCTGAA-5'
5'-...GAGTATGCTGAGTGTAAGTCGCTTGAGCTGCCGGATTCAAGCGACTT-3'
```

```
                              AATCC
                  5'-AAGTCGCTTG      G       5' hairpin structure
3'-...CTCATACGACTCACATTCAGCGAAC      G          (top strand)
                              TCGAC
```

```
                              TTAGG
                  3'-TTCAGCGAAC      C       3' hairpin structure
5'-...GAGTATGCTGAGTGTAAGTCGCTTG      C          (bottom strand)
                              AGCTG
```

```
support
      GAGTGT-3'
                              AATCC
                  5'-AAGTCGCTTG      G       5' hairpin structure
3'-...CTCATACGACTCACATTCAGCGAAC      G       Ligates to
                              TCGAC          3' immobilized probe
```

```
support
      CTCACA-5'
                              TTAGG
                  3'-TTCAGCGAAC      C       3' hairpin structure
5'-...GAGTATGCTGAGTGTAAGTCGCTTG      C       Ligates to
                              AGCTG          5' immobilized probe
```

Figure 6

5'-...TATACGAAATCCGGGATGGATTTAGCATACCTGTTGGTCGGTAAGTGCCCG...-3'
3'-...ATATGCTTTAGGCCCTACCTAAATCGTATGGACAACCAGCCATTCACGGGC...-5'

↓ Restriction digestion

5'-...TATACGAAATCCGGGATGGATTTAGCA         TACCTGTTGGTCGGTAAGTGCCCG...-3'
3'-...ATATGCTTTAGGCCCTACCTAAATCGTATGG         ACAACCAGCCATTCACGGGC...-5'

↓ Mix with adaptor-indexer

5'-...TATACGAAATCCGGGATGGATTTAGCA         TACCCGCTTGAGCTGCCGGA-3'
3'-...ATATGCTTTAGGCCCTACCTAAATCGTATGG         GCGAACTCGACGGCCT-5'

↓ Ligation

5'-...TATACGAAATCCGGGATGGATTTAGCATACCCGCTTGAGCTGCCGGA-3'
3'-...ATATGCTTTAGGCCCTACCTAAATCGTATGGGCGAACTCGACGGCCT-5'

↓ Hybridization to hairpin primer

5'-...GGGATGGATTTAGCATACCCGCTTGAGCTGCCGGA-3'
              3'-ATGGGCGAACTCGACGGCCT
                                    AAGTTCGCTGAA-5'

↓ Amplification

5'-...GGGATGGATTTAGCATACCCGCTTGAGCTGCCGGATTCAAGCGACTT-3'
3'-...CCCTACCTAAATCGTATGGGCGAACTCGACGGCCTAAGTTCGCCCAT-5'

↓ Hairpin formation (bottom strand)

AATCC
                      5'-TACCCGCTTG        G
       3'-...CCCTACCTAAATCGTATGGGCGAAC        G
                                        TCGAC

↓ Mix with detector array support
              TTAGCA-3'
                                        AATCC
                      5'-TACCCGCTTG        G
       3'-...CCCTACCTAAATCGTATGGGCGAAC        G
                                        TCGAC ↓ Ligation support                         AATCC
              TTAGCATACCCGCTTG        G
       3'-...CCCTACCTAAATCGTATGGGCGAAC        G
                                        TCGAC

SEQUENCE LISTING

```
<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Description of Artificial  Sequence: Note =
      synthetic construct
<221> NAME/KEY: misc_feature
<222> LOCATION: 1-18
<223> OTHER INFORMATION: n = g,a,c, or t( u)

<400> SEQUENCE: 1
ggatgnnntt agcatacc                                                 18

<210> SEQ ID NO 2
<211> LENGTH: 32
<212> TYPE: DNA
<213> ORGANISM: Artificial Sequence
<220> FEATURE:
<223> OTHER INFORMATION: Description of Artificial  Sequence: hairpin
      primer

<400> SEQUENCE: 2
aagtcgcttg aatccggcag ctcaagcgac tt                                 32

<210> SEQ ID NO 3
<211> LENGTH: 43
<212> TYPE: DNA
<213> ORGANISM: Artificial Sequence
<220> FEATURE:
<223> OTHER INFORMATION: Description of Artificial  Sequence: nucleic
      acid fragment
```

-continued

<400> SEQUENCE: 3
gagtatgctg agtgtaagtc gcttgagctg ccggacagac ctt                            43

<210> SEQ ID NO 4
<211> LENGTH: 47
<212> TYPE: DNA
<213> ORGANISM: Artificial Sequence
<220> FEATURE:
<223> OTHER INFORMATION: Description of Artificial  Sequence: amplified
      nucleic acid fragment

<400> SEQUENCE: 4
gagtatgctg agtgtaagtc gcttgagctg ccggattcaa gcgactt                        47

<210> SEQ ID NO 5
<211> LENGTH: 51
<212> TYPE: DNA
<213> ORGANISM: Artificial Sequence
<220> FEATURE:
<223> OTHER INFORMATION: Description of Artificial  Sequence: nucleotide
      fragment

<400> SEQUENCE: 5
tatacgaaat ccgggatgga tttagcatac ctgttggtcg gtaagtgccc g                   51

<210> SEQ ID NO 6
<211> LENGTH: 20
<212> TYPE: DNA
<213> ORGANISM: Artificial Sequence
<220> FEATURE:
<223> OTHER INFORMATION: Description of Artificial  Sequence: compatible
      adaptor-indexer

<400> SEQUENCE: 6
tacccgcttg agctgccgga                                                      20

<210> SEQ ID NO 7
<211> LENGTH: 47
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 7
tatacgaaat ccgggatgga tttagcatac ccgcttgagc tgccgga                        47

<210> SEQ ID NO 8
<211> LENGTH: 12
<212> TYPE: DNA
<213> ORGANISM: Artificial Sequence
<220> FEATURE:
<223> OTHER INFORMATION: Description of Artificial  Sequence: hairpin
      primer

<400> SEQUENCE: 8
aagtcgcttg aa                                                              12

<210> SEQ ID NO 9
<211> LENGTH: 47
<212> TYPE: DNA
<213> ORGANISM: Artificial Sequence
<220> FEATURE:
<223> OTHER INFORMATION: Description of Artificial  Sequence: Nucleotide
      fragment

<400> SEQUENCE: 9

```
gggatggatt tagcataccc gcttgagctg ccggattcaa gcgactt            47
```

<210> SEQ ID NO 10
<211> LENGTH: 33
<212> TYPE: DNA
<213> ORGANISM: Artificial Sequence
<220> FEATURE:
<223> OTHER INFORMATION: Description of Artificial  Sequence: Note =
      synthetic construct
<221> NAME/KEY: misc_feature
<222> LOCATION: 1-33
<223> OTHER INFORMATION: n = g,a,c, or t( u)

<400> SEQUENCE: 10

```
cagcagnnnn nnnnnnnnnn nnnnnnnnnn nnn                           33
```

<210> SEQ ID NO 11
<211> LENGTH: 40
<212> TYPE: DNA
<213> ORGANISM: Artificial Sequence
<220> FEATURE:
<223> OTHER INFORMATION: Description of Artificial  Sequence: Nucleotide
      fragment

<400> SEQUENCE: 11

```
tctagtccaa tccaagctac atcagcagat gcggactaga                    40
```

<210> SEQ ID NO 12
<211> LENGTH: 57
<212> TYPE: DNA
<213> ORGANISM: Artificial Sequence
<220> FEATURE:
<223> OTHER INFORMATION: Description of Artificial  Sequence: Note =
      synthetic construct
<221> NAME/KEY: misc_feature
<222> LOCATION: 1-57
<223> OTHER INFORMATION: n = g,a,c, or t( u)

<400> SEQUENCE: 12

```
nnnnnnnnnn ngacctgtct agtccgcatc tgctgatgta gcttggattg g actaga    57
```

<210> SEQ ID NO 13
<211> LENGTH: 23
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 13

```
cgcacgggct atagctgata tag                                      23
```

<210> SEQ ID NO 14
<211> LENGTH: 31
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 14

```
ggcaaatgtc tagtccgaaa tccaagctat g                             31
```

<210> SEQ ID NO 15
<211> LENGTH: 34
<212> TYPE: DNA
<213> ORGANISM: Artificial Sequence

```
<220> FEATURE:
<223> OTHER INFORMATION: Description of Artificial  Sequence: Nucleotide
      fragment

<400> SEQUENCE: 15
tctagtccga atgtagcttg gatttcggac taga                                34

<210> SEQ ID NO 16
<211> LENGTH: 20
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 16
tgcccgatct cgactatatc                                                20

<210> SEQ ID NO 17
<211> LENGTH: 42
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 17
ccgtttacag atcaggcttt aggttcgatg taagcctgat ct                       42

<210> SEQ ID NO 18
<211> LENGTH: 28
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 18
cggtggatga cttgaagcta tgcttagg                                       28

<210> SEQ ID NO 19
<211> LENGTH: 48
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 19
cggtggatga cttgaagcta tgcggtatta cagcctatat accgcata                 48

<210> SEQ ID NO 20
<211> LENGTH: 16
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 20
caaatgtcta gtccga                                                    16

<210> SEQ ID NO 21
<211> LENGTH: 59
<212> TYPE: DNA
<213> ORGANISM: Artificial Sequence
<220> FEATURE:
```

<223> OTHER INFORMATION: Description of Artificial  Sequence: Note =
      synthetic construct
<221> NAME/KEY: misc_feature
<222> LOCATION: 1-59
<223> OTHER INFORMATION: n = g,a,c, or t( u)

<400> SEQUENCE: 21
gacctgtcta gtccaatcca agctacatca gcagatgcgg actagacagg t cnnnnnnn        59

<210> SEQ ID NO 22
<211> LENGTH: 54
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 22
tgaagctatg cggtatatag gctgtaatac cgcatagctt caagtcatcc a ccg             54

<210> SEQ ID NO 23
<211> LENGTH: 18
<212> TYPE: DNA
<213> ORGANISM: Artificial Sequence
<220> FEATURE:
<223> OTHER INFORMATION: Description of Artificial  Sequence: Note =
      synthetic construct
<221> NAME/KEY: misc_feature
<222> LOCATION: 1-18
<223> OTHER INFORMATION: n = g,a,c, or t( u)

<400> SEQUENCE: 23
catagcttca nnncatcc                                                      18

<210> SEQ ID NO 24
<211> LENGTH: 8
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 24 cgcatggg                                                                  8

<210> SEQ ID NO 25
<211> LENGTH: 8
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 25 atagcttg                                                                  8

<210> SEQ ID NO 26
<211> LENGTH: 16
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 26
caagctatgg atccga                                                        16

```
<210> SEQ ID NO 27
<211> LENGTH: 28
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 27
caagctatgg atctggtatt acagccta                                        28

<210> SEQ ID NO 28
<211> LENGTH: 30
<212> TYPE: DNA
<213> ORGANISM: Artificial Sequence
<220> FEATURE:
<223> OTHER INFORMATION: Description of Artificial  Sequence: hairpin
      primer

<400> SEQUENCE: 28
ggatctggta taggctgtaa taccagatcc                                      30

<210> SEQ ID NO 29
<211> LENGTH: 38
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 29
caagctatgg atctggtatt acagcctata ccagatcc                             38

<210> SEQ ID NO 30
<211> LENGTH: 44
<212> TYPE: DNA
<213> ORGANISM: Artificial Sequence
<220> FEATURE:
<223> OTHER INFORMATION: Description of Artificial  Sequence: nucleic
      acid fragment

<400> SEQUENCE: 30
agctatggat ctggtatagg ctgtaatacc agatccatag cttg                      44

<210> SEQ ID NO 31
<211> LENGTH: 53
<212> TYPE: DNA
<213> ORGANISM: Artificial Sequence
<220> FEATURE:
<223> OTHER INFORMATION: Description of Artificial  Sequence: probe

<400> SEQUENCE: 31
ttagcatacc cgcttgaatc cggcagctca agcgggtatg ctaaatccat c cc           53

<210> SEQ ID NO 32
<211> LENGTH: 53
<212> TYPE: DNA
<213> ORGANISM: Artificial Sequence
<220> FEATURE:
<223> OTHER INFORMATION: Description of Artificial  Sequence: probe

<400> SEQUENCE: 32
gagtgtaagt cgcttgaatc cggcagctca agcgacttac actcagcata c tc           53

<210> SEQ ID NO 33
<211> LENGTH: 21
<212> TYPE: DNA
```

-continued

```
<213> ORGANISM: Artificial Sequence
<220> FEATURE:
<223> OTHER INFORMATION: Description of Artificial Sequence: nucleic
      acid fragment

<400> SEQUENCE: 33
gccatggatc tctcacatgg g                                              21
```

ANALYSIS OF SEQUENCE TAGS WITH HAIRPIN PRIMERS

CROSS-REFERENCE TO RELATED APPLICATIONS

This application is a continuation-in-part of U.S. Application Ser. No. 09/544,713, filed Apr. 6, 2000, U.S. Pat. No. 6,261,782. This application claims benefit of U.S. Provisional Application No. 60/148,870, filed Aug. 13, 1999, by Paul M. Lizardi and Darin R. Latimer, entitled "Analysis Of Sequence Tags With Hairpin Primers." Application Ser. No. 09/544,713, filed Apr. 6, 2000, and Application Ser. No. 60/148,870, filed Aug. 13, 1999, are hereby incorporated herein by reference.

BACKGROUND OF THE INVENTION

The disclosed invention is generally in the field of nucleic acid characterization and analysis, and specifically in the area of analysis and comparison of gene expression patterns and genomes.

The study of differences in gene-expression patterns is one of the most promising approaches for understanding mechanisms of differentiation and development. In addition, the identification of disease-related target molecules opens new avenues for rational pharmaceutical intervention. Currently, there are two main approaches to the analysis of molecular expression patterns: (1) the generation of mRNA-expression maps and (2) examination of the 'proteome', in which the expression profile of proteins is analyzed by techniques such as two-dimensional gel electrophoresis or mass spectrometry (matrix-assisted-desorption-ionization-time-of-flight (MALDI-TOF)) and by the ability to sequence sub-picomole amounts of protein. Classical approaches to transcript imaging, such as northern blotting or plaque hybridization, are time-consuming and material-intensive ways to analyze mRNA-expression patterns. For these reasons, other methods for high-throughput screening in industrial and clinical research have been developed.

A breakthrough in the analysis of gene expression was the development of the northern-blot technique in 1977 (Alwine et al., *Proc. Natl. Acad. Sci. U.S.A*. 74:5350–5354 (1977)). With this technique, labeled cDNA or RNA probes are hybridized to RNA blots to study the expression patterns of mRNA transcripts. Alternatively, RNase-protection assays can detect the expression of specific RNAs. These assays allow the expression of mRNA subsets to be determined in a parallel manner. For RNase-protection assays, the sequence of the analyzed mRNA has to be known in order to synthesize a labeled cDNA that forms a hybrid with the selected mRNA; such hybrids resist RNA degradation by a single-strand-specific nuclease and can be detected by gel electrophoresis. As a third approach, differential plaque-filter hybridization allows the identification of specific differences in the expression of cloned cDNAs (Maniatis et al. *Cell* 15:687–701 (1978)). Although all of these techniques are excellent tools for studying differences in gene expression, the limiting factor of these classical methods is that expression patterns can be analyzed only for known genes.

The analysis of gene-expression patterns made a significant advance with the development of subtractive cDNA libraries, which are generated by hybridizing an mRNA pool of one origin to an mRNA pool of a different origin. Transcripts that do not find a complementary strand in the hybridization step are then used for the construction of a cDNA library (Hedrick et al., *Nature* 308:149–153 (1984)). A variety of refinements to this method have been developed to identify specific mRNAs (Swaroop et al., *Nucleic Acids Res*. 25:1954 (1991); Diatchenko et al, *Proc. Natl. Acad. Sci. U.S.A* 93:6025–6030 (1996)). One of these is the selective amplification of differentially expressed mRNAs via biotin- and restriction-mediated enrichment (SABRE; Lavery et al., *Proc. Natl. Acad. Sci. U.S.A*. 94:6831–6836 (1997)), cDNAs derived from a tester population are hybridized against the cDNAs of a driver (control) population. After a purification step specific for tester-cDNA-containing hybrids, tester-tester homohybrids are specifically amplified using an added linker, thus allowing the isolation of previously unknown genes.

The technique of differential display of eukaryotic mRNA was the first one-tube method to analyze and compare transcribed genes systematically in a bi-directional fashion; subtractive and differential hybridization techniques have only been adapted for the unidirectional identification of differentially expressed genes (Liang and Pardee, *Science* 257:967–971 (1992)). Refinements have been proposed to strengthen reproducibility, efficiency, and performance of differential display (Bauer et al., *Nucleic Acids Res*. 11:4272–4280 (1993); Liang and Pardee, *Curr. Opin. Immunol* 7:274–280 (1995); Ito and Sakaki, *Methods Mol. Biol*. 85:37–44 (1997); Praschar and Weissman, *Proc. Natl. Acad. Sci U.S.A*. 93;659–663 (1996), Shimkets et al., *Nat Biotechnol*, 17: 798–803 (1999)). Although these approaches are more reproducible and precise than traditional PCR-based differential display, they still require the use of gel electrophoresis, and often implies the exclusion of certain DNA fragments from analysis.

Originally developed to identify differences between two complex genomes, representational difference analysis (RDA) was adapted to analyze differential gene expression by taking advantage of both subtractive hybridization and PCR (Lisitsyn et al., *Science* 259:946–951 (1993); Hubank and Schatz, *Nucleic Acids Res*. 22:5640–5648 (1994)). In the first step, mRNA derived from two different populations, the tester and the driver (control), is reverse transcribed; the tester cDNA represents the cDNA population in which differential gene expression is expected to occur. Following digestion with a frequently cutting restriction endonuclease, linkers are ligated to both ends of the cDNA. A PCR step then generates the initial representation of the different gene pools. The linkers of the tester and driver cDNA are digested and a new linker is ligated to the ends of the tester cDNA. The tester and driver cDNAs are then mixed in a 1:100 ratio with an excess of driver cDNA in order to promote hybridization between single-stranded cDNAs common in both tester and driver cDNA pools. Following hybridization of the cDNAs, a PCR exponentially amplifies only those homoduplexes generated by the tester cDNA, via the priming sites on both ends of the double-stranded CDNA (O'Neill and Sinclair, *Nucleic Acids Res*. 25:2681–2682 (1997); Wada et al., *Kidney Int*. 51:1629–1638 (1997); Edman et al., *J*. 323:113–118 (1997)).

The gene-expression pattern of a cell or organism determines its basic biological characteristics. In order to accelerate the discovery and characterization of mRNA-encoding sequences, the idea emerged to sequence fragments of cDNA randomly, direct from a variety of tissues (Adams et al., *Science* 252:1651–1656 (1991); Adams et al., *Nature* 377:3–16 (1995)). These expressed sequence tags (ESTs) allow the identification of coding regions in genome-derived sequences. Publicly available EST databases allow the comparative analysis of gene expression by computer. Differentially expressed genes can be identified by comparing the databases of expressed sequence tags of a given organ or cell type with sequence information from a different origin (Lee et al., *Proc. Natl. Acad. Sci. U.S.A.* 92:8303–8307 (1995); Vasmatzis et al., *Proc. Natl. Acad. Sci. U.S.A.* 95:300–304 (1998)). A drawback to sequencing of ESTs is the requirement for large-scale sequencing facilities.

Serial analysis of gene expression (SAGE) is a sequence-based approach to the identification of differentially expressed genes through comparative analyses (Velculescu et al., *Science* 270:484–487 (1995)). It allows the simultaneous analysis of sequences that derive from different cell population or tissues. Three steps form the molecular basis for SAGE: (1) generation of a sequence tag (10–14 bp) to identify expressed transcripts; (2) ligation of sequence tags to obtain concatemers that can be cloned and sequenced; and (3) comparison of the sequence data to determine differences in expression of genes that have been identified by the tags. This procedure is performed for every MRNA population to be analyzed. A major drawback of SAGE is the fact that corresponding genes can be identified only for those tags that are deposited in gene banks, thus making the efficiency of SAGE dependent on the extent of available databases. Alternatively, a major sequencing effort is required to complete a SAGE data set capable of providing 95% coverage of any given mRNA population, simply because most of the sequencing work yields repetitive reads on those tags that are present in high frequency in cellular mRNA. In other words, SAGE sequencing experiments yield diminishing returns for rare mRNAs, whose unique tags will begin to accumulate in the database only after many weeks of sequencing effort.

A different approach to the study of gene-expression profiles and genome composition is the use of DNA microarrays. Current DNA microarrays are systematically gridded at high density. Such microarrays are generated by using cDNAs (for example, ESTs), PCR products or cloned DNA, which are linked to the surface of nylon filters, glass slides or silicon chips (Schena et al., *Science* 270, 467–470 (1995). DNA arrays can also be assembled from synthetic oligonucleotides, either by directly applying the synthesized oligonucleotides, either by directly applying the synthesized oligonucleotides to the matrix or by a more sophisticated method that combines photolithography and solid-phase chemical synthesis (Fodor et al., *Nature* 364:555–556 (1993)). To determine differences in gene-expression, labeled cDNAs or oligonucleotides are hybridized to the DNA-or oligomer-carrying arrays. When using different fluorophores for labeling cDNAs or oligonucleotides, two probes can be applied simultaneously to the array and compared at different wavelengths. The expression of 10,000 genes and more can be analyzed on a single chip (Chee et al., *Science* 274:610–614 (1996)). However, depending on the sensitivity of both cDNA and oligonucleotide arrays, the intensity of hybridization signals can leave the linear range when either weakly or abundantly expressed genes are analyzed. Thus, individual optimization steps are required to ensure the accurate detection of differentially expressed genes. While such microarray methods may be used to address a number of interesting biological questions, they are not suitable for the discovery of new genes.

There is a need for a method that combines the power and convenience of array hybridization technology with the capability for gene discovery inherent in differential display or SAGE. Such a method would be most attractive if it could enable comprehensive gene expression analysis without the use of gel electrophoresis, and without the need for a redundant DNA sequencing effort.

Therefore, it is an object of the present invention to provide a method for the comprehensive analysis of nucleic acid sequence tags.

It is another object of the present invention to provide a detector composition that allows indexing of nucleic acid sequence tags.

It is another object of the present invention to provide a method for sequence-based detection of nucleic acid fragments of interest.

BRIEF SUMMARY OF THE INVENTION

Disclosed is a method for the comprehensive analysis of nucleic acid samples and a detector composition for use in the method. The method involves amplifying nucleic acid fragments of interest using a primer that can form a hairpin structure; sequence-based coupling of the amplified fragments detector probes; and detection of the coupled fragments. The amplified fragments are coupled by hybridization and covalent coupling, preferably by ligation, to a detector probe. The probe is preferably immobilized in an array or on sortable beads. A hairpin structure formed at the end of the amplified fragments facilitates coupling of the fragments to the probes. The method allows detection of the fragments where detection provides some sequence information about the fragments. The method allows a complex sample of nucleic acid to be cataloged quickly and easily in a reproducible and sequence-specific manner. The method can also be used to detect amplified fragments having a known sequence.

BRIEF DESCRIPTION OF THE DRAWINGS

FIG. 1A and FIG. 1B are a listing of examples of hairpin primers and the hairpin structure that forms from the resulting hairpin ligator incorporated at the end of an amplified fragment. Nucleotides in one of the strands of the stem of the hairpin structure are represented by H. Nucleotides in the primer sequence of the hairpin primer are represented by p and P. Nucleotides in the part of the primer sequence involved in one of the strands of the stem of the hairpin structure are represented by P. Nucleotides in the fragment are represented by f and F. Nucleotides in the part of the fragment sequence involved in one of the strands of the stem of the hairpin structure are represented by F. Other nucleotides in the hairpin primer (that is, nucleotides that are neither part of the stem nor part of the primer sequence) are represented by n. In the hairpin ligator for hairpin primer 10, which represents an example of a hairpin primer used with adaptor-indexers, nucleotides in the primer sequence corresponding to sticky end sequences are boldface, nucleotides corresponding to adaptor-indexer sequences are underlined, and the recognition sequence of the restriction endonuclease (FokI in this example) is listed as CCTAC.

FIG. 4 is a diagram examples of an amplified fragment (SEQ ID NO:4), the hairpin structures that can be formed from the hairpin ligators in the fragment strands, and the detector probes to which the hairpin ligators can be ligated. The diagram illustrates the relationship of an amplified fragment to the formation of 5' hairpin structures and 3' hairpin structures and the relationship of the polarity of a hairpin structure and the polarity of the detector probe to which it can be ligated.

FIG. 6 is a diagram of nucleic acid molecules used and formed during an example of the disclosed method using adaptor-indexers. Ligation of the top strand of the amplified fragment is illustrated. The restriction enzyme recognition sequence is underlined and the sticky end sequence is in bold. The fragment (SEQ ID NO:5) is shown at the top of the diagram. Depicted in order from top to bottom are the nucleic acid molecule after cleavage with FokI; the nucleic acid fragment (left) and an example of a compatible adaptor-indexer (SEQ ID NO:6; right); the adaptor-indexer ligated to the nucleic acid fragment (SEQ ID NO:7); the hairpin primer (SEQ ID NO:8) hybridized to the top strand of the adaptor/fragment (nucleotides 13–47 of SEQ ID NO:7); the fragment after amplification (SEQ ID NO:9); the hairpin structure formed by the bottom strand of the amplified fragment; the hairpin structure mixed with the probe array (showing the relevant detector probe); and the fragment ligated to the probe array (SEQ ID NO:31). The fragment sequence determined in this example is GGATGNNNTTAGCATACC (SEQ ID NO:1).

DETAILED DESCRIPTION OF THE INVENTION

Figure 2:
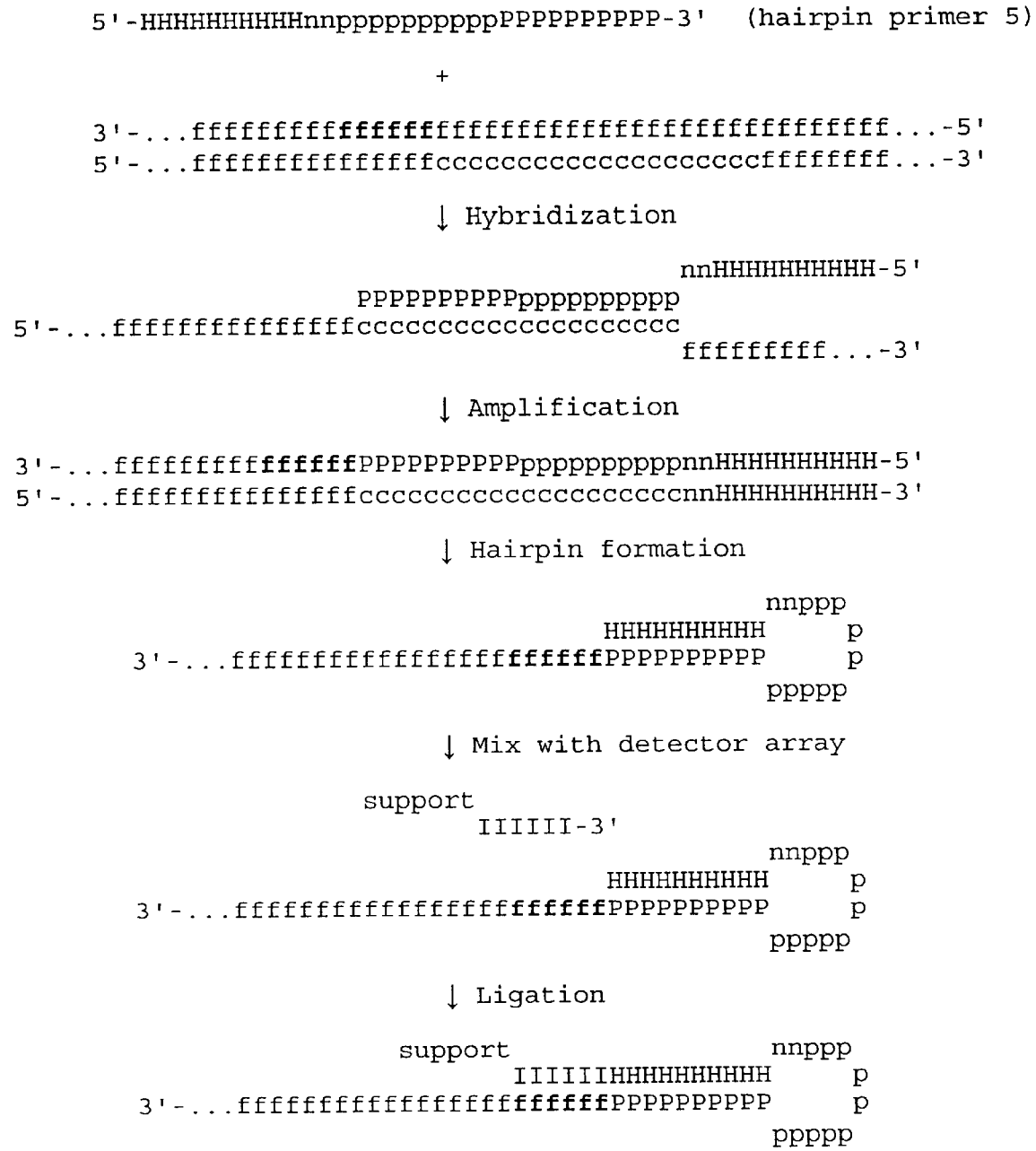
FIG. 2 is a diagram of nucleic acid molecules used and formed during an example of the disclosed method using generic sequences. Ligation of the top strand of the amplified fragment is illustrated. Nucleotides in one of the strands of the stem of the hairpin structure are represented by H. Nucleotides in the primer sequence of the hairpin primer are represented by p and P. Nucleotides in the part of the primer sequence involved in one of the strands of the stem of the hairpin structure are represented by P. Nucleotides in the fragment are represented by c, f, and F. Nucleotides in the part of the fragment sequence involved in one of the strands of the stem of the hairpin structure are represented by F. Nucleotides in the fragment complementary to the primer sequence of the hairpin primer are represented by c. Nucleotides in the detector probe are represented by I. Nucleotides in the fragment complementary to the detector probe are represented by f (boldface). Other nucleotides in the hairpin primer (that is, nucleotides that are neither part of the stem nor part of the primer sequence) are represented by n.

The disclosed method allows a complex sample of nucleic acid to be quickly and easily cataloged in a reproducible and sequence-specific manner. Such a catalog can be compared with other, similarly prepared catalogs of other nucleic acid samples to allow convenient detection of differences between the samples. The catalogs, which incorporate information about the nucleic acid samples, can serve as fingerprints of the nucleic acid samples which can be used both for detection of related nucleic acid samples and comparison of nucleic acid samples. For example, the presence or identity of specific organisms can be detected by producing a catalog of nucleic acid of the test organism and comparing the resulting catalog with reference catalogs prepared from known organisms. Changes and differences in gene expression patterns can also be detected by preparing catalogs of mRNA from different cell samples and comparing the catalogs. The catalog of sequences can also be used to produce a set of probes or primers that is specific for the source of a nucleic acid sample.

Comparison of nucleic acid catalogs produced with the disclosed method is facilitated by the highly ordered nature of the sequence information produced and cataloged in the method. Use of immobilization, sorting, and/or array detection in the method allows automation of the method, the cataloging of the information, and comparisons to other catalogs. The method results in the equivalent of a large number of sequence-specific bins that can be filled, empty, or filled to different levels, with the pattern of filled and empty bins, and/or the amount of signal in a bin, providing information about the nucleic acid sample that has been cataloged.

The disclosed method also allows specific and sensitive detection of nucleic acid fragments of interest. The use of sequence-based covalent coupling in the detection increases the reliability of detection over detection methods based only on probe hybridization. The disclosed method is also more efficient and less time consuming than conventional nucleic acid sequencing techniques.

One embodiment of the disclosed method involves the following basic steps. Where multiple different primer sequences are used, the nucleic acid sample is preferably divided into aliquots (referred to as index samples) before amplification. Preferably, the nucleic acid sample is divided into as many aliquots as the number of primer sequences used. Preferred nucleic acid samples for use in the disclosed method are samples to which adapter-indexers have been coupled. Where a single primer sequence is used, the nucleic acid sample is preferably not divided into index samples. Each index sample is then mixed with a different hairpin primer, each of which has a different primer sequence. For PCR amplification, a second primer is also mixed with each index sample. It is preferred that the second primer not be a hairpin primer. The index samples are then amplified.

Next, the index samples are treated to allow formation of hairpin structures at the fragment ends containing hairpin primer sequences. This is preferably accomplished by digesting one of the strands of the amplified fragments.

Finally, the index samples are reacted with and coupled to detector probes. It is preferred that the probes include every possible sequence of a given length (for example, every possible six base sequence). The ends of the detector probes and the hairpin ends are coupled only if the probe hybridizes adjacent to the end of the hairpin ligator. Preferably each index sample is reacted with a different probe array. Coupling can be accomplished using any suitable technique, including ligation and chemical reactions. Ligation is preferred. When coupling is by ligation, there should be a 5'-phosphate capable of participating in ligation on the appropriate strand.

Each processed DNA fragment from the sample will result in a signal based on coupling of an amplified fragment to a probe. A complex nucleic acid sample will produce a unique pattern of signals. It is this pattern that allows unique cataloging of nucleic acid samples and sensitive and powerful comparisons of the patterns of signals produced from different nucleic acid samples. The detector probe to which a DNA fragment is coupled identifies the sequence of the DNA fragment to which the primer hybridized and the adjacent sequence of the DNA fragment to which the detector probe hybridized.

Coupling of amplified fragments to probes can be detected directly or indirectly. For example, any of the probe or the amplified fragment can be detected. Association of an amplified fragment with a given probe is indicative of coupling of the probe and the amplified fragment. Detection of such associations can be facilitated through immobilization of the probes or hairpin primers, and through the use of capture tags, sorting tags and detectable labels in association with the probes, hairpin primers, and/or amplified fragments. Any combination of immobilization and association with capture tags, sorting tags, and labels can be used. Preferably, the probes are immobilized in arrays and the amplified fragments are associated with a detectable label. Thus, detection of a signal at a particular location in a particular array of detector probes can provide information about nucleic acid fragments indexed from the nucleic acid sample.

Where the probes are immobilized in arrays, the array, and location in the array, where a DNA fragment generates a signal identify the sequence of the DNA fragment. The same effect can be accomplished by otherwise capturing, sorting, or detecting particular probes (via capture tags, sorting tags, and labels). That is, so long as the probe and the DNA fragment coupled to it can be identified, a pattern can be determined.

A preferred form of the disclosed method uses nucleic acid fragments to which adapter-indexers have been covalently coupled for amplification using hairpin primers. The manner in which the adaptor-indexers are coupled to nucleic acid fragments results in indexing of different fragments and preservation of sequence information about the fragments. Adaptor-indexes are coupled to nucleic acid fragments using the following basic steps. A nucleic acid sample is cleaved with one or more nucleic acid cleaving reagents (preferably restriction endonucleases) that results in a set of DNA fragments having sticky ends with a variety of sequences. The sample may also be divided into aliquots (referred to as index samples); preferably as many aliquots as there are sticky end sequences. Where multiple nucleic acid cleaving reagents are used, the nucleic acid sample is preferably divided into index samples before digestion. Where a single nucleic acid cleaving reagent is used, the nucleic acid sample is preferably divided into index samples following digestion. Each index sample is then mixed with a different adaptor-indexer, each of which has a sticky end compatible with one of the possible sticky ends on the DNA fragments in that index sample. The adaptor-indexes are then covalently coupled to compatible DNA fragments.

Each index sample can then be cleaved with one or more other nucleic acid cleaving reagents (referred to as second nucleic acid cleaving reagents), preferably a restriction enzyme having a four base recognition sequence. A second adaptor can then be covalently coupled to the DNA fragments in the index samples. The DNA fragments are then amplified using hairpin primers as described above. For this form of the method, it is preferred that the primer sequences of the hairpin primers are complementary to sequences in the adaptor-indexers.

Materials

Nucleic Acid Samples

Any nucleic acid sample can be used with the disclosed method. Examples of suitable nucleic acid samples include genomic samples, mRNA samples, cDNA samples, nucleic acid libraries (including cDNA and genomic libraries), whole cell samples, environmental samples, culture samples, tissue samples, bodily fluids, and biopsy samples. Numerous other sources of nucleic acid samples are known or can be developed and any can be used with the disclosed method. Preferred nucleic acid samples for use with the disclosed method are nucleic acid samples of significant complexity such as genomic samples, cDNA samples, and mRNA samples.

Nucleic acid fragments are segments of larger nucleic molecules. Nucleic acid fragments, as used in the disclosed method, generally refer to nucleic acid molecules that have been amplified or that have been cleaved. A nucleic acid sample that has been amplified is referred to as an amplified sample. A nucleic acid sample that has been cleaved using a nucleic acid cleaving reagent is referred to as a digested sample.

An index sample is a nucleic acid sample that has been divided into different aliquots for further processing. In the context of the disclosed method, index samples are preferably aliquots of a nucleic acid sample to which different hairpin primers will be added. In the disclosed method, different nucleic acid fragments are processed in the different index samples based on the primer sequences of the hairpin primers. Thus, it is preferred that nucleic acid samples be divided into as many index samples as the number of hairpin primers used for amplification.

A control nucleic acid sample is a nucleic acid sample to which another nucleic acid sample (which can be referred to as a tester nucleic acid sample) is to be compared. A control index sample is an index sample to which another index sample (which can be referred to as a tester index sample) is to be compared.

Secondary index samples are aliquots of index samples. Thus, index samples can be divided into a plurality of secondary index samples. Secondary index samples are to be cleaved with a nucleic acid cleaving reagent, preferably a restriction enzyme. Restricted index samples and non-restricted index samples are aliquots of index samples. Restricted index samples are to be cleaved with a nucleic acid cleaving reagent while non-restricted index samples are not. Restricted secondary index samples and non-restricted secondary index samples are aliquots of secondary index samples. Restricted secondary index samples are to be cleaved with a nucleic acid cleaving reagent while non-restricted secondary index samples are not. Secondary index samples, restricted index samples, non-restricted index samples, restricted secondary index samples, and non-restricted secondary index samples are referred to collectively herein as derivative index samples. Each is derived from an index sample and, in some cases, from another derivative index sample.

Hairpin Primers

A hairpin primer is a nucleic acid molecule that contains a primer sequence and that can form a stem-loop or hairpin structure. For convenience, and unless otherwise indicated, both hairpin structures and stem-loop structures are referred to herein as hairpin structures. The base paired portion of a hairpin structure is referred to as the stem of the hairpin structure. Hairpin primers are used in the disclosed method as specialized amplification primers that, following amplification, can form a hairpin structure at the end on amplified nucleic acid fragments. The hairpin is designed to allow sequence-specific covalent coupling of a detector probe to the end of the hairpin based on the adjacent sequence of the amplified fragment. The primer sequence of a hairpin primer is at the 3' end of the hairpin primer. The stem of a hairpin primer can involve all or part of the primer sequence. Although it is preferred, the stem need not extend to the 3' end of the primer sequence. The stem can also extend into the sequence of the amplified fragment. It is preferred that the stem of a hairpin primer involves all of the primer sequence without extending into the sequence of the amplified fragment.

Where fragments containing adaptor-indexers are amplified, it is preferred that the primer sequence of the hairpin primers be complementary to sequences in the adaptor-indexer. The stem of a hairpin primer can involve all or part of the sticky end sequence (or recognition sequence) for which the adaptor-indexer is designed. Although it is preferred, the stem need not extend to the 3' end of the sticky end sequence (or recognition sequence). The stem can also extend into the sequence of the amplified fragment beyond the sticky end sequence (or recognition sequence). It is preferred that the stem of a hairpin primer involves all of the sticky end sequence (or recognition sequence) without extending further into the sequence of the amplified fragment. Some examples of hairpin structures of hairpin primers and their relationships to amplified nucleic acids are illustrated in FIG. 1. Hairpin primers 1 and 4–9 are examples of hairpin primers where the stem extends to the end of the primer sequence. Hairpin primer 2 is an example of a hairpin primer where the stem does not extend to the end of the primer sequence. Hairpin primer 3 is an example of a hairpin primer where the stem extends into the sequence of the amplified fragment. Hairpin primer 9 is an example of a hairpin primer where the stem involves all of the primer sequence. Hairpin primers 1–8 are examples of hairpin primers where the stem does not involve all of the primer sequence. Hairpin primers 1–5 are examples of hairpin primers where the stem is 10 base pairs long. Hairpin primer 6 is an example of a hairpin primer where the stem is 12 base pairs long. Hairpin primer 7 is an example of a hairpin primer where the stem is 8 base pairs long. Hairpin primer 8 is an example of a hairpin primer where the stem is 3 base pairs long. Hairpin primer 9 is an example of a hairpin primer where the stem is 16 base pairs long.

Amplification using hairpin primers results in amplified nucleic acid fragments having hairpin primer sequences at one or both ends of the fragments. These hairpin primer sequences in amplified fragments are referred to as hairpin ligators. The hairpin ligators can form hairpin structures. A hairpin structure with a 3' end is referred to as a 3' hairpin structure and a hairpin structure with a 5' end is referred to as a 5' hairpin structure (hairpin ligators containing these structures are referred to as 3' hairpin ligators and 5' hairpin ligators, respectively).

The stem of a hairpin structure can have any length that allows formation of the hairpin structure and which is of sufficient stability to allow covalent coupling of a detector probe. Preferably, the stem of the hairpin structure of a hairpin ligator is from 3 to 16 base pairs long, and more preferably from 6 to 10 base pairs long.

Generally, the sequence of the stem portion of a hairpin primer should not include the recognition sequence of any nucleic acid cleaving reagent to be used in a subsequent step in the method. However, inclusion of restriction sites in hairpin primers is useful in some embodiments of the disclosed method. For example, hybridization of the fragments to detector probes can be aided by shortening the fragment length prior to hybridization. This can be accomplished, for example, by digesting the fragment with a restriction endonuclease or other nucleic acid cleaving reagent. Preferably, the recognition site for the nucleic acid cleaving reagent is included in the sequence of the hairpin primer. For this purpose, it is preferred that the nucleic acid cleaving reagent used has a cleavage site offset from the recognition site. An example of such a nucleic acid cleaving reagent is the restriction enzyme EcoP15I.

Hairpin primers can contain labile nucleotides, preferably in the loop, that allow the hairpin structure to be broken. For example, uracil rather than thymine can be used in hairpin primers (phosphoramidite chemicals available from Glenn Research). When used in conjunction with uracil-DNA glycosylase (UDG; available from New England Biolabs) can be used to introduce specific strand breaks.

It is preferred that hairpin primers not have additional sequences that are self-complementary, other than the self-complementary stem portion. It is considered that this condition is met if there are no complementary regions greater than six nucleotides long without a mismatch or gap.

While the hairpin primers (and amplified nucleic acid fragments) can be detected using sequence-based detection systems, the hairpin primers (or amplified nucleic acid fragments) can also contain a label to facilitate detection. Numerous labels are known and can be used for this purpose.

Hairpin primers can also contain or be associated with capture tags to facilitate immobilization or capture of fragments in which hairpin primers have been incorporated. In general, the capture tag can be one member of a binding pair such as biotin and streptavidin. Capture tags are discussed more fully elsewhere herein. Hairpin primers can also contain or be associated with sorting tags to facilitate sorting or separation of fragments in which hairpin primers have been incorporated. In general, the sorting tag can be a detectable label such as a fluorescent moiety or a manipulable moiety such as a magnetic bead. Sorting tags are discussed more fully elsewhere herein. Hairpin primers can also be immobilized on a substrate.

Hairpin primers can also include a few phosphorothioate linkages or other non-hydrolyzable bonds at the 5' end to protect the strand of the amplified fragment containing the hairpin primer from exonuclease digestion. This allows one of the strands of the amplified fragments to be degraded. Hairpin primers can also include one or more photocleavable nucleotides to facilitate release of probe sequences and amplified fragments coupled to the probe. Photocleavable nucleotides and their use are described in WO 00/04036.

Hairpin primers need not be composed of naturally occurring nucleotides. Modified nucleotides, unnatural bases and nucleotide and oligonucleotide analogs can be used. All that is required is that the primer have the general structure described herein and be capable of the interactions and reactions required in the disclosed method.

Detector Probes

Detector probes are molecules, preferably oligonucleotides, that can hybridize to nucleic acids in a sequence-specific manner. In the disclosed method, detector probes are used to capture nucleic acid fragments amplified using the disclosed hairpin primers based on complementary sequences present in the amplified nucleic acid fragments. Detector probes are preferably used in sets having a variety of probe sequences, preferably a set of probes having every possible combination (or hybridizable to every combination) of nucleotide sequence the length of the probe. Detector probes are preferably used in sets where each probe has the same length. Preferred lengths for the probe portion of detector probes are five, six, seven, and eight nucleotides. Detector probes preferably include a probe portion (for hybridization to sample fragments) and linker portions through which the probe portion is coupled to a substrate, capture tag, sorting tag, or label. These linker portions can have any suitable structure and will generally be chosen based on the method of immobilization or synthesis of the detector probes. The linker portion can be made up of or include nucleotides. The linker portions can have any suitable length and preferably are of sufficient length to allow the probe portion to hybridize effectively. For convenience and unless otherwise indicated, reference to the length of detector probes refers to the length of the probe portion of the probes. Immobilized detector probes are detector probes immobilized on a support.

Detector probes can be, and preferably are, immobilized on a substrate. Detector probes can also contain or be associated with capture tags to facilitate immobilization or capture of the probes and amplified fragments to which they have been coupled. Detector probes can also contain or be associated with sorting tags to facilitate sorting or separation of the probes and amplified fragments to which they have been coupled. Detector probes can also contain or be associated with labels to facilitate detection of the probes and amplified fragments to which they have been coupled.

Detector probes can also include one or more photocleavable nucleotides to facilitate release of probe sequences and amplified fragments coupled to the probe. Photocleavable nucleotides and their use are described in WO 00/04036.

Detector probes need not be composed of naturally occurring nucleotides. Modified nucleotides, unnatural bases and nucleotide and oligonucleotide analogs can be used. All that is required is that the probe have the general structure described herein and be capable of the interactions and reactions required in the disclosed method.

Probe Arrays

Different detector probes can be used together as a set. The set can be used as a mixture of all or subsets of the probes, probes used separately in separate reactions, or immobilized in an array. Probes used separately or as mixtures can be physically separable through, for example, the use of capture tags, sorting tags, or immobilization on beads. A probe array (also referred to herein as an array) includes a plurality of probes immobilized at identified or predetermined locations on the array. In this context, a plurality of probes refers to a multiple probes each having a different sequence. Each predetermined location on the array has one type of probe (that is, all the probes at that location have the same sequence). Each location will have multiple copies of the probe. The spatial separation of probes of different sequence in the array allows separate detection and identification of amplified fragments that become coupled to the probes via hybridization of the probes to nucleic acid fragments in a nucleic acid sample. If an amplified fragment is detected at a given location in a probe array, it indicates that the sequence adjacent to the site in the nucleic acid fragment where the fragment hybridized is complementary to the probe immobilized at that location in the array.

Adaptor-indexers can also be immobilized in arrays. Different modes of the disclosed method can be performed with different components immobilized, labeled, or tagged. Arrays of adaptor-indexers can be made and used as described below and elsewhere herein for the detector probes.

Preferably, the detector probes in a probe array will all be of the same polarity. That is, each probe will have a free 5' end or each probe will have a free 3' end. The polarity of a probe determines to which form of hairpin structure the probe can be coupled. A probe array with probes having 5' ends is referred to as a 5' probe array. A probe array with probes having 3' ends is referred to as a 3' probe array. A probe array can also have probes of both polarities. If so, it is preferred that probes of different polarities be immobilized at identified or predetermined locations on the probe array.

Solid-state substrates for use in probe array can include any solid material to which oligonucleotides can be coupled, directly or indirectly. This includes materials such as acrylamide, cellulose, nitrocellulose, glass, silicon, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Methods for immobilization of oligonucleotides to solid-state substrates are well established. Detector probes can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Methods for producing arrays of oligonucleotides on solid-state substrates are also known. Examples of such techniques are described in U.S. Pat. No. 5,871,928 to Fodor et al., U.S. Pat. No. 5,654,413 to Brenner, U.S. Pat. No. 5,429,807, and U.S. Pat. No. 5,599,695 to Pease et al.

Although preferred, it is not required that a given probe array be a single unit or structure. The set of probes may be distributed over any number of solid supports. For example, at one extreme, each probe may be immobilized in a separate reaction tube or container.

The probes in arrays can also be designed to have similar hybrid stability. This would make hybridization of fragments to detector probes more efficient and reduce the incidence of mismatch hybridization. The hybrid stability of probes can be calculated using known formulas and principles of thermodynamics (see, for example, Santa Lucia et al., *Biochemistry* 35:3555–3562 (1996); Freier et al., *Proc. Natl. Acad. Sci. USA* 83:9373–9377 (1986); Breslauer et al., *Proc. Natl. Acad. Sci. USA* 83:3746–3750 (1986)). The hybrid stability of the probes can be made more similar (a process that can be referred to as smoothing the hybrid stabilities) by, for example, chemically modifying the probes (Nguyen et al., *Nucleic Acids Res.* 25(15):3059–3065 (1997); Hohsisel, *Nucleic Acids Res.* 24(3):430–432 (1996)). Hybrid stability can also be smoothed by carrying out the hybridization under specialized conditions (Nguyen et al., *Nucleic Acids Res.* 27(6):1492–1498 (1999); Wood et al., *Proc. Natl. Acad. Sci. USA* 82(6):1585–1588 (1985)).

Another means of smoothing hybrid stability of the probes is to vary the length of the probes. This would allow adjustment of the hybrid stability of each probe so that all of the probes had similar hybrid stabilities (to the extent possible). Since the addition or deletion of a single nucleotide from a probe will change the hybrid stability of the probe by a fixed increment, it is understood that the hybrid stabilities of the probes in a probe array will not be equal. For this reason, similarity of hybrid stability as used herein refers to any increase in the similarity of the hybrid stabilities of the probes (or, put another way, any reduction in the differences in hybrid stabilities of the probes). This is useful since any such increased similarity in hybrid stability can improve the efficiency and fidelity of hybridization and coupling of the detector probes.

The efficiency of hybridization and coupling of detector probes to sample fragments can also be improved by grouping detector probes of similar hybrid stability in sections or segments of a probe array that can be subjected to different hybridization conditions. In this way, the hybridization conditions can be optimized for particular classes of probes.

Second Primers

A second primer is a nucleic acid molecule that contains a primer sequence. The primer sequence of a second primer is at the 3' end. A second primer differs from a hairpin primer in that a second primer is not designed to form a hairpin structure. Second primers are used to amplify the opposite strand of nucleic acid fragments when the amplification technique requires a second primer (and when a second hairpin primer is not used to amplify the opposite strand). Where fragments containing second adaptors are amplified, it is preferred that the primer sequence of the second primers (or the second hairpin primers, if used) be complementary to sequences in the second adaptor.

Second primers can also contain detector sequences 5' of the primer sequences. Such detector sequences can be used to facilitate detection of nucleic acid fragments amplified in the disclosed method. Detector sequences can have any arbitrary sequence, preferably sequences that do not interfere with operation of the method. For example, it is preferred that detector sequences be chosen that are not significantly complementary to sequences in the second primer or sequences in hairpin primers or other second primers. Detector sequences are preferably the same. Also preferred are sets of second primers where the detector sequences within a set are the same but which differ between sets.

Second primers can also contain or be associated with capture tags to facilitate immobilization or capture of fragments in which second primers have been incorporated. Capture tags are discussed more fully elsewhere herein. Second primers can also contain or be associated with sorting tags to facilitate sorting or separation of fragments in which second primers have been incorporated. Sorting tags are discussed more fully elsewhere herein. Second primers can also contain or be associated with labels to facilitate detection of fragments in which second primers have been incorporated. Second primers can also be immobilized on a substrate.

Second primers can also include one or more photocleavable nucleotides to facilitate release of second primer sequences for detection. Photocleavable nucleotides and their use are described in WO 00/04036.

Second primers need not be composed of naturally occurring nucleotides. Modified nucleotides, unnatural bases and nucleotide and oligonucleotide analogs can be used. All that is required is that the second primer have the general structure described herein and be capable of the interactions and reactions required in the disclosed method.

Labels

To aid in detection and quantitation of fragments coupled to detector probes, labels can be incorporated into, coupled to, or associated with hairpin primers, second primers, detector probes, and/or the fragments. A label is any molecule that can be associated with nucleic acid fragments, directly or indirectly, and which results in a measurable, detectable signal, either directly or indirectly. A label is associated with a component when it is coupled or bound, either covalently or non-covalently, to the component. A label is coupled to a component when it is covalently coupled to the component. Many suitable labels for incorporation into, coupling to, or association with nucleic acid are known. Examples of labels suitable for use in the disclosed method are radioactive isotopes, fluorescent molecules, phosphorescent molecules, bioluminescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuceinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are preferred form of labor since they can be directly incorporated into nucleic acids during synthesis. Examples of labels that can be incorporated into DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringer Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [$3.3.1.1^{3,7}$]decane]-4-yl) phenyl phosphate; Tropix, Inc.).

Other labels include molecular or metal barcodes, mass labels, and labels detectable by nuclear magnetic resonance, electron paramagnetic resonance, surface enhanced raman scattering, surface plasmon resonance, fluorescence, phosphorescence, chemiluminescence, resonance raman, microwave, or a combination. Mass labels are compounds or moieties that have, or which give the labeled component, a distinctive mass signature in mass spectroscopy. Mass labels are useful when mass spectroscopy is used for detection. Preferred mass labels are peptide nucleic acids and carbohydrates. Combinations of labels can also be useful. For example, color-encoded microbeads having, for example, 265 unique combinations of labels, are useful for distinguishing numerous components. For example, 256 different detector probes can be uniquely labeled and detected allowing mutiplexing and automation of the disclosed method.

Useful labels are described in de Haas et al., "Platinum porphyrins as phosphorescent label for time-resolved microscopy," *J. Histochem. Cytochem.* 45(9):1279–92 (1997); Karger and Gesteland, "Digital chemiluminescence imaging of DNA sequencing blots using a charge-coupled device camera," *Nucleic Acids Res.* 20(24):6657–65 (1992); Keyes et al., "Overall and internal dynamics of DNA as monitored by five-atom-tethered spin labels," *Biophys. J.* 72(1):282–90 (1997); Kirschstein et al., "Detection of the DeltaF508 mutation in the CFTR gene by means of time-resolved fluorescence methods," *Bioelectrochem. Bioenerg.* 48(2):415–21 (1999); Kricka, "Selected strategies for improving sensitivity and reliability of immunoassays," *Clin. Chem.* 40(3):347–57 (1994); Kricka, "Chemiluminescent and bioluminescent techniques," *Clin. Chem.* 37(9):1472–81 (1991); Kumke et al., "Temperature and quenching studies of fluorescence polarization detection of DNA hybridization," *Anal. Chem.* 69(3):500–6 (1997); McCreery, "Digoxigenin labeling," *Mol. Biotechnol.* 7(2):121–4 (1997); Mansfield, et al., "Nucleic acid detection using non-radioactive labeling methods," *Mol. Cell Probes* 9(3):145–56 (1995); Nurmi, et al., "A new label technology for the detection of specific polymerase chain reaction products in a closed tube," *Nucleic Acids Res.* 28(8):28 (2000); Oetting et al. "Multiplexed short tandem repeat polymorphisms of the Weber 8A set of markers using tailed primers and infrared fluorescence detection,"*Electrophoresis* 19(18):3079–83(1998); Roda et al., "Chemiluminescent imaging of enzyme-labeled probes using an optical microscope-videocamera luminograph," *Anal. Biochem.* 257(1):53–62 (1998); Siddiqi et al., "Evaluation of electrochemiluminescence- and bioluminescence-based assays for quantitating specific DNA," *J. Clin. Lab. Anal.* 10(6):423–31 (1996); Stevenson et al., "Synchronous luminescence: a new detection technique for multiple fluorescent probes used for DNA sequencing," *Biotechniques* 16(6):1104–11 (1994); Vo-Dinh et al., "Surface-enhanced Raman gene probes," *Anal. Chem.* 66(20):3379–83 (1994); Volkers et al., "Microwave label detection technique for DNA in situ hybridization," *Eur. J. Morphol.* 29(1):59–62 (1991).

Metal barcodes, a form of molecular barcode, are 30–300 nm diameter by 400–4000 nm multilayer multi metal rods. These rods are constructed by electrodeposition into an alumina mold, then the alumina is removed leaving these small multilayer objects behind. The system can have up to 12 zones encoded, in up to 7 different metals, where the metals have different reflectivity and thus appear lighter or darker in an optical microscope depending on the metal; this leads to practically unlimited identification codes. The metal bars can be coated with glass or other material, and probes attached to the glass using methods commonly known in the art; assay readout is by fluorescence from the target, and the identity of the probe is from the light dark pattern of the barcode.

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled. In another form of detection, labels can be distinguished temporally via different fluorescent, phosphorescent, or chemiluminescent emission lifetimes. Multiplexed time-dependent detection is described in Squire et al., J. Microscopy 197(2):136–149 (2000), and WO 00/08443.

Quantitative measurement of the amount or intensity of a label can be used. For example, quantitation can be used to determine if a given label, and thus the labeled component, is present at a threshold level or amount. A threshold level or amount is any desired level or amount of signal and can be chosen to suit the needs of the particular form of the method being performed.

Nucleic Acid Cleaving Reagents

Some forms of the disclosed method make use of nucleic acid cleaving reagents. Nucleic acid cleaving reagents are compounds, complexes, and enzymes that cause, mediate, or catalyze cleavage on nucleic acid molecules. Preferred nucleic acid cleaving reagents are those that cleave nucleic acid molecules in a sequence-specific manner. Restriction enzymes (also referred to as restriction endonucleases) are the preferred form of nucleic acid cleaving reagents. Other nucleic acid cleaving reagents include the universal restriction endonucleases of Szybalski (Szybalski, *Gene* 40(2–3):169–73 (1985); Podhajska and Szybalski, *Gene* 40(2–3):175–82 (1985)[published erratum appears in Gene 43(3):325 (1985)]), the advanced DNA cleavage systems developed by Breaker et al. (Carmi et al., *Proc Natl Acad Sci U S A* 95(5):2233–2237 (1998)), and the use of zinc fingers to direct site recognition of restriction enzymes such as the hybrid restriction enzymes described by Kim et al., *Proc. Natl. Acad. Sci. USA* 93(3):1156–1160 (1996), and Smith et al., *Nucleic Acids Res.* 27(2):674–681 (1999).

Many nucleic acid cleaving reagents are known and can be used with the disclosed method. Relevant to the disclosed method, nucleic acid cleaving reagents generally have a recognition sequence and a cleavage site. Many nucleic acid cleaving reagents, especially restriction enzymes, also generate sticky ends at the cleavage site. A recognition sequence is the nucleotide sequence which, if present in a nucleic acid molecule, will direct cleavage of the nucleic acid molecule by a cognate nucleic acid cleaving reagent. The cleavage site of a nucleic acid cleaving reagent is the site, usually in relation to the recognition sequence, where the nucleic acid cleaving reagent cleaves a nucleic acid molecule. Sticky ends (also referred to as cohesive ends, protruding ends, and 5' or 3' overhangs) are single-stranded nucleic acid segments at the end of a double-stranded nucleic acid segment.

For specific embodiments of the method, the nucleic acid cleaving reagents used will have certain properties and/or certain relationships to other restriction enzymes used in the method. For example, in some preferred embodiments of the disclosed method, nucleic acid cleaving reagents that generates sticky ends having a plurality of different sequences are preferred, with nucleic acid cleaving reagents having a cleavage site offset from the recognition sequence being most preferred. Other embodiments of the disclosed method require the use of different nucleic acid cleaving reagents that have different recognition sequences and/or generate different sticky ends than other nucleic acid cleaving reagents used on the same index sample at other stages in the method. For example, where three digests (that is, cleavage reactions) are used in the method, it is preferred that the nucleic acid cleaving reagents used in each of the digests have a recognition sequence different from that of the nucleic acid cleaving reagents used in the other digests. In such cases, the known properties of nucleic acid cleaving reagents can be used to select or design appropriate nucleic acid cleaving reagents.

Where a nucleic acid cleaving reagent cleaves DNA at a site different or offset from the recognition sequence, a variety of sticky ends having different sequences can be generated. This is because recognition sequences in nucleic acids can occur next to any sequence and therefore the site of cleavage can have any sequence. For example, FokI cleaves 9 (upper strand) and 13 (lower strand) nucleotides downstream from the recognition site of GGATG. The four base sticky end will have whatever sequence happens to be 10 to 13 nucleotides away from the recognition site. Given enough cleavage sites, a total of 256 different sticky end sequences (that is every possible four base sequence) can result from a FokI digestion. As a result, restriction enzymes such as Type IIS restriction enzymes can be said to generate sticky ends having a plurality of different sequences.

As used herein, unless otherwise indicated, the terms digest, digestion, digested, and digesting refer generally to a cleavage reaction or the act of cleaving and is not intended to be limited to cleavage by a protein enzyme or by any particular mechanism. Similarly, the term restricted is intended to refer to any nucleic acid cleavage, not just cleavage by a restriction enzyme. In the context of nucleic acid cleaving reagents, sequence-specific requires only some sequence specificity, not absolute sequence specificity. That is, nucleic acid cleaving reagents having a completely or partially defined recognition sequence are preferred. Thus, nucleic acid cleaving reagents having some degeneracy in their recognition sequence are still considered sequence-specific.

A second nucleic acid cleaving reagent is a nucleic acid cleaving reagent used to digest a secondary index sample. A third nucleic acid cleaving reagent is an nucleic acid cleaving reagent used to digest a restricted index sample or a restricted secondary index sample. Second and third nucleic acid cleaving reagents are preferably Type II restriction endonucleases that cleave in the recognition sequence. A second restriction enzyme is a restriction enzyme used to digest a secondary index sample. A third restriction enzyme is an enzyme used to digest a restricted index sample or a restricted secondary index sample. Second and third restriction enzymes are preferably Type II restriction endonucleases that cleave in the recognition sequence.

In addition to the use of restriction enzymes in a standard mode, one can make use of the Type IIS enzymes as universal restriction endonuclease as described by Szybalski (Szybalski, Gene 40(2–3):169–73 (1985); Podhajska and Szybalski, Gene 40(2–3):175–82 (1985)[published erratum appears in Gene 43(3):325 (1985)]). In the Szybalski technique single stranded or double stranded DNA can be cleaved at any arbitrary (but specific) site utilizing the structure described in combination with a Type IIS enzyme. More advanced DNA cleavage systems have been evolved by Breaker et al. (Carmi et al., Proc Natl Acad Sci U S A 95(5):2233–2237 (1998)). In these systems Breaker has shown that DNA recognize a particular sequence in a target DNA and can cleave the target DNA, single stranded or double stranded targets. With Breaker's system for evolution of DNA for a particular action, it is clear that given reasonable time and effort a suitable DNA for a recognition and particular cleavage result is practical.

Adaptor-Indexers

Adaptor-indexers are double-stranded nucleic acids containing a single-stranded portion and a double-stranded portion. The single-stranded portion is at one end of the adaptor-indexer and constitutes a sticky end. The sticky end is referred to as the sticky end portion of the adaptor-indexer. It is preferable that the protruding single strand (sticky end) have two, three, four, or five nucleotides. The double-stranded portion of adaptor-indexers may have any convenient sequence or length. In general, the sequence and length of the double-stranded portion is selected to be adapted to subsequent steps in the method. For example, sequences in the adaptor-indexer may be used for primer or probe hybridization. A main purpose of adaptor-indexers is to provide sequence for hybridization by a hairpin primer for amplification. Thus, preferred sequence composition and length for the double-stranded portion of adaptor-indexers will generally be those that are useful for hairpin primer hybridization. Adaptor-indexers can also include a detector portion which is designed to facilitate detection of the adaptor-indexer. The detection portion can be, for example, a sequence that is a hybridization target or it can be a label or tag.

Generally, the sequence of the double-stranded portion of an adaptor-indexer should not include the recognition sequence of any restriction enzyme to be used in a subsequent step in the method. It is preferred that adaptor-indexers not have any sequences that are self-complementary. It is considered that this condition is met if there are no complementary regions greater than six nucleotides long without a mismatch or gap.

A set of adaptor-indexers for use in the disclosed method should include different adaptor-indexers where the single-stranded portion each have a different nucleotide sequence selected from combinations and permutations of the nucleotides A, C, G, and T. Where multiple nucleic acid cleaving reagents are used in the first digest, the single-stranded portion of each adaptor-indexer can have a different nucleotide sequence compatible with a sticky end sequence generated by one of the nucleic acid cleaving reagents. While the sticky ends of adaptor-indexers in one set have different sequences, it is preferred that they be of the same length to facilitate use of the set to index fragments produced by cleavage by one nucleic acid cleaving reagent. It is preferable that the members of a set of adaptor-indexers contain a double-stranded portion which is identical for each member of the set.

A preferred set of indexing linker strands comprising: (a) at least two single-stranded first oligonucleotides each having a common identical sequence, and a unique sequence of a length selected from 2, 3, 4 and 5 nucleotides selected from permutations and combinations of A, G, C and T nucleotides, at one end selected from a 3' end and a 5' end; and (b) a single stranded second oligonucleotide whose sequence is complementary to the common sequence of the first oligonucleotides such that, when hybridized with any one of the first oligonucleotides, a double-stranded adaptor-indexer would result which includes an end having a sticky end with a unique sequence.

Adaptor-indexers can also contain or be associated with capture tags to facilitate immobilization or capture of fragments to which adaptor-indexers have been coupled. In general, the capture tag can be one member of a binding pair such as biotin and streptavidin. Capture tags are discussed more fully elsewhere herein. Adaptor-indexers can also contain or be associated with sorting tags to facilitate sorting or separation of fragments to which adaptor-indexers have been coupled. In general, the sorting tag can be a detectable label such as a fluorescent moiety or a manipulable moiety such as a magnetic bead. Sorting tags are discussed more fully elsewhere herein. Adaptor-indexers can also contain or be associated with labels to facilitate detection of fragments to which adaptor-indexers have been coupled. Adaptor-indexers can also be immobilized on a substrate. Adaptor-indexers can also include a protruding end at the end opposite the sticky end. Such an end can be used as, for example, a hybridization target for a label to be associated with the adaptor-indexer (and thus can be considered the detection portion of the adaptor-indexer). Adaptor-indexers can also include one or more photocleavable nucleotides to facilitate release of adaptor-indexer sequences for detection. Photocleavable nucleotides and their use are described in WO 00/04036.

Adaptor-indexers need not be composed of naturally occurring nucleotides. Modified nucleotides, unnatural bases and nucleotide and oligonucleotide analogs can be used. All that is required is that the adaptor-indexer have the general structure described herein and be capable of the interactions and reactions required in the disclosed method.

Second Adaptors

Second adaptors are double-stranded nucleic acids containing a single-stranded portion and a double-stranded portion. The single-stranded portion is at one end of the second adaptor and constitutes a sticky end. It is preferable that the protruding single strand (sticky end) have two, three, four, or five nucleotides. The double-stranded portion of second adaptor may have any convenient sequence or length. In general, the sequence and length of the double-stranded portion is selected to be adapted to subsequent steps in the method. For example, the second adaptors can provide sequence for primer hybridization of a second primer or second hairpin primer. Thus, preferred sequence composition and length for the double-stranded portion of second adaptors will generally be those that are useful for primer hybridization.

Generally, the sequence of the double-stranded portion of a second adaptor should not include the recognition sequence of any nucleic acid cleaving reagent to be used in a subsequent step in the method. It is preferred that second adaptors not have any sequences that are self-complementary. It is considered that this condition is met if there are no complementary regions greater than six nucleotides long without a mismatch or gap.

A set of second adaptors for use in the disclosed method can include different second adaptors where the single-stranded portion each have a different nucleotide sequence compatible with a sticky end sequence generated by one of the second restriction enzymes. It is preferable that the members of a set of second adaptors contain a double-stranded portion which is identical for each member of the set.

Second adaptors can also contain or be associated with capture tags to facilitate immobilization or capture of fragments to which second adaptors have been coupled. Second adaptors can also contain or be associated with sorting tags to facilitate sorting or separation of fragments to which second adaptors have been coupled. Second adaptors can also contain or be associated with labels to facilitate detection of fragments to which second adaptors have been coupled. Second adaptors can also be immobilized on a substrate.

Capture Tags

A capture tag is any compound that can be used to separate compounds or complexes having the capture tag from those that do not. Preferably, a capture tag is a compound, such as a ligand or hapten, that binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

Preferred capture tags, described in the context of nucleic acid probes, are described by Syvnen et al., *Nucleic Acids Res.*, 14:5037 (1986). Preferred capture tags include biotin, which can be incorporated into nucleic acids. In the disclosed method, capture tags incorporated into adaptor-indexers or second adaptors can allow sample fragments (to which the adaptors have been coupled) to be captured by, adhered to, or coupled to a substrate. Similarly, capture tags incorporated into hairpin primers or second primers can allow sample fragments (into which the primers have been incorporated) to be captured, adhered to, or coupled to a substrate. Such capture allows simplified washing and handling of the fragments, and allows automation of all or part of the method.

Capturing sample fragments on a substrate may be accomplished in several ways. In one embodiment, capture docks are adhered or coupled to the substrate. Capture docks are compounds or moieties that mediate adherence of a sample fragment by binding to, or interacting with, a capture tag on the fragment. Capture docks immobilized on a substrate allow capture of the fragment on the substrate. Such capture provides a convenient means of washing away reaction components that might interfere with subsequent steps.

Substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Preferred forms of substrates are plates and beads. The most preferred form of beads are magnetic beads.

In one embodiment, the capture dock is an oligonucleotide. Methods for immobilizing and coupling oligonucleotides to substrates are well established. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

In another embodiment, the capture dock is an anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Sorting Tags

A sorting tag is any compound that can be used to sort or separate compounds or complexes having the sorting tag from those that do not. In general, all capture tags can be a sorting tag. Sorting tags also include compounds and moieties that can be detected and which can mediate the sorting of tagged components. Such forms of sorting tags are generally not also capture tags. For example, a fluorescent moiety can allow sorting of components tagged with the moiety from those that are not (or those with a different tag). However, such a fluorescent moiety does not necessarily have a suitable capture dock with which it can interact and be captured. Preferably, a sorting tag is a label, such as a fluorescent label, that can mediate sorting.

Method

The disclosed method involves the following basic steps. A nucleic acid sample is subjected to amplification using primers where at least one of the primers is a hairpin primer. Nucleic acids in the sample are amplified to result in amplified nucleic acid fragment having hairpin primer sequences at one or both ends. These hairpin primer sequences in amplified fragments are referred to as hairpin ligators. The amplified fragments are treated to allow the hairpin ligators to form stem-loop or hairpin structures at the end of the amplified fragments. The amplified fragments are then contacted with a plurality of detector probes and the amplified fragments are covalently coupled to probes via the hairpin ligator. Coupled fragments can then be detected. Since the sequence of the amplified fragment adjacent to the hairpin structure of the hairpin ligator determines the sequence of the detector probe to which the hairpin ligator is coupled, this adjacent sequence in the amplified fragment is identified by noting to which probe a given fragment is coupled. This identification is preferably accomplished by having probes of known sequence immobilized at known locations in the probe array.

In one embodiment of the disclosed method, a catalog of nucleic acid sequences in a nucleic acid sample can be created by using multiple hairpin primers, each with a different primer sequence, to amplify the nucleic acid sample. Multiple different nucleic acid fragments will be amplified with different sequences adjacent to the hairpin structure of the hairpin ligator. The pattern of fragments on the probe array provides a catalog of the fragments that can then be compared with other nucleic acid samples.

Where multiple hairpin primers are used, the nucleic acid sample is preferably divided into aliquots (referred to as index samples) before amplification. Each index sample is then mixed with a different hairpin primer, each of which has a primer sequence. The hairpin primers then mediate amplification of different nucleic acid sequences (based on the sequence of the primer sequence).

Each index sample can be amplified with one or more second primers (in conjunction with a hairpin primer). The hairpin primer amplifies one strand and the second primer amplifies the opposite strand. All index samples are preferably amplified with the same second primer(s). Alternatively, the index samples can be further divided into secondary index samples with each amplified with a different second primer or set of second primers. Amplified fragments in each index sample (or secondary index sample) would then have primer sequences at each end. The sequences of these primers can be used as primer binding sites for further amplification of the fragments, preferably once the fragments are coupled to detector probes.

Figure 5:
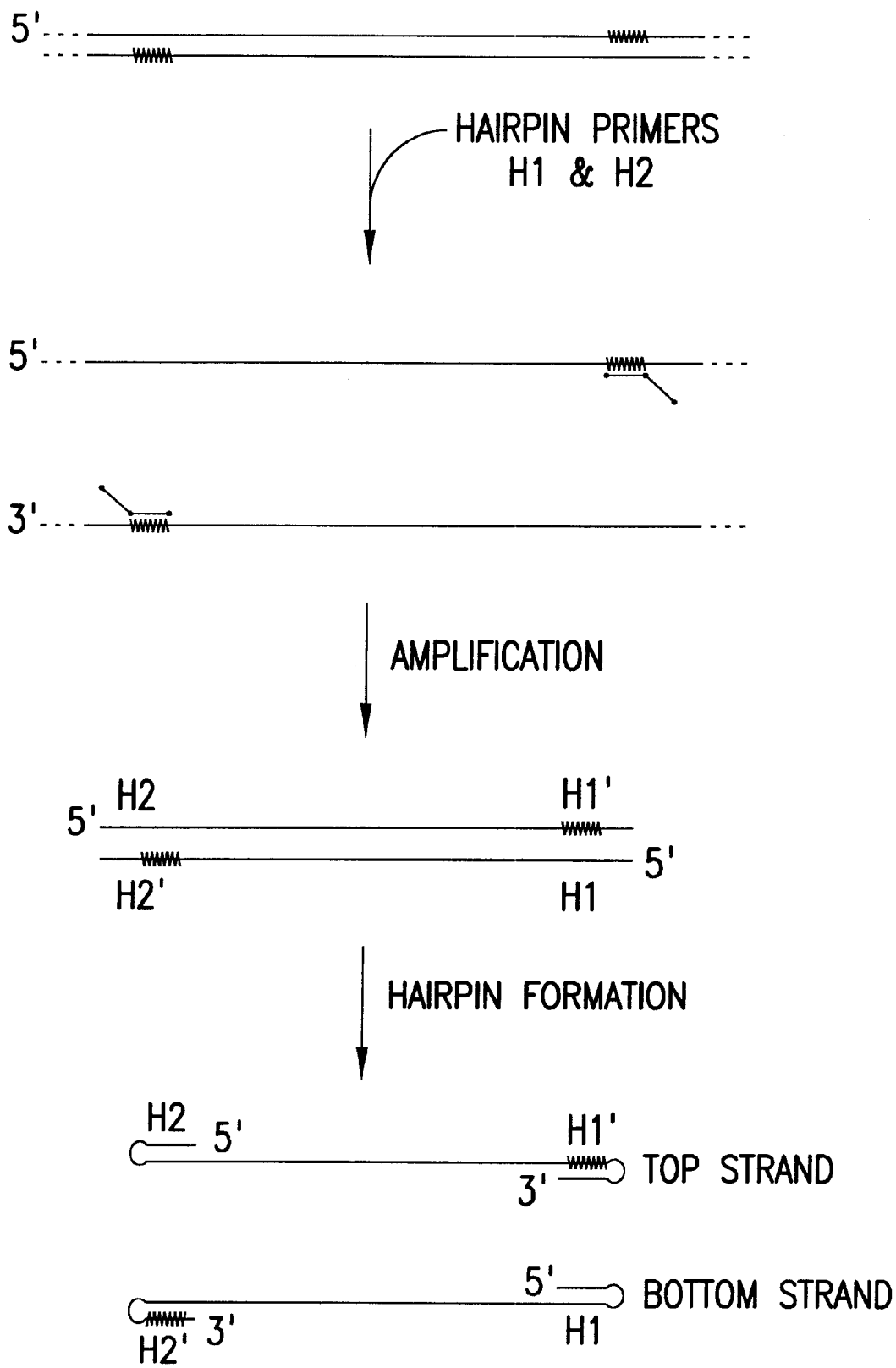
FIG. 5 is a diagram of an example of the disclosed method where hairpin primers are used to prime amplification of both strands of a nucleic acid molecule. Each strand of the resulting amplified fragment has a hairpin ligator at each end and a hairpin structure of opposite polarity can form at each end of both strands.

Different strands of the amplified fragments can subjected to covalent coupling on a probe array. Since one of the strands will produce a hairpin structure with a 3' end and the other strand will produce a hairpin structure with a 5' end (see FIG. 4), differential coupling of the strands can be accomplished by the simple expedient of using a probe array with detector probes all of the same polarity—that is, detector probes all with 5' ends (in a 5' probe array) or detector probes all with 3' ends (in a 3' probe array). Only the fragment strand with compatible polarity can be coupled to the detector probe. A hairpin structure with a 3' end is referred to as a 3' hairpin structure and a hairpin structure with a 5' end is referred as a 5' hairpin structure (hairpin ligators containing these structures are referred to as 3' hairpin ligators and 5' hairpin ligators, respectively). Selective strand coupling can also be accomplished, for example, by digesting one of the strands with an exonuclease (detector probes of the correct polarity must still be used). Such digestion is also preferred since it reduces the chance for interference by the opposite strand during coupling to the detector probes.

Where a nucleic acid sample is amplified using multiple hairpin primers having different primer sequences, both ends of the amplified fragments will have hairpin ligators (see FIG. 5, bottom). Thus, both strands will form both a 5' hairpin structure and a 3' hairpin structure and both stands can be coupled to detector probes. By subjecting both strands of such fragments to both a 5' probe array and a 3' probe array, both ends of both strands of each fragment can be detected and cataloged. This provides a maximum of information about the nucleic acid sample.

Figure 3:
FIG. 3 is a diagram of nucleic acid molecules used and formed during an example of the disclosed method using specific sequences. Ligation of the top strand of the amplified fragment is illustrated. Nucleotides in the fragment complementary to the detector probe are boldface. Depicted from top to bottom are the hairpin primer (SEQ ID NO:2), the nucleic acid fragment (SEQ ID NO:3), the hairpin primer hybridized to bottom strand of the nucleic acid fragment, the amplified nucleic acid fragment (SEQ ID NO:4), the hairpin structure formed in the top strand of the amplified nucleic acid fragment, and the amplified nucleic acid strand ligated to a detector probe (SEQ ID NO:32). The molecules and structures of FIG. 3 can be directly compared with those of FIG. 2 to identify sequences in FIG. 3 having particular significance.

Each sample (or each index sample or derivative index sample) can be reacted with and coupled to an array of detector probes. Preferred arrays include every possible sequence of a given length (for example, every possible six base sequence), although arrays containing fewer combinations can also be used. Such arrays are referred to herein as probe arrays. The ends of the detector probes and the hairpin ligator are coupled together only if the detector probe hybridizes adjacent to the end of the hairpin ligator. Thus, a hairpin ligator is coupled to an detector probe on the array only when a sequence complementary to the detector probe is present immediately adjacent to the end of the stem sequence in an amplified fragment. Examples of the relationship and interaction of various components of the disclosed method are illustrated in FIGS. 2 and 3.

Each amplified fragment from the sample will result in a signal at a particular location in a particular array of detector probes. The probe array in which the signal for a given fragment is detected is determined by the primer sequence of the hairpin primer. Where multiple hairpin primers (having different primer sequences) are used, each different primer sequence is preferably processed in a separate index sample and a separate probe array is preferably used for each index sample or derivative index sample. The location in the probe array in which the signal for a given fragment is detected is determined by the sequence in the fragment immediately adjacent to the end of the stem sequence in the fragment since the detector probe must hybridize to this sequence in order to be coupled to the hairpin ligator of the fragment. A complex nucleic acid sample will produce a unique pattern of signals on the probe arrays. It is this pattern that allows unique cataloging of nucleic acid samples and sensitive and powerful comparisons of the patterns of signals produced from different nucleic acid samples.

The use of different sets of hairpin primers provides a means for generating different subsets of fragments from a complex sample. Such a defined subset of molecules may be further resolved by additional amplification and indexing, or by any of the established techniques such as cloning, PCR amplification, or gel electrophoresis. Individual members of the class may be distinguished by identifying characteristics such as length, sequence, or restriction endonuclease maps. The sequence of the primers sequences of the hairpin ligators provides a means of indexing a large number of nucleic acid fragments.

Detector probes of different sequence can be immobilized at different locations on the probe array. In this way, the sequence of the detector probes on the probe array and the sequence of nucleic acid fragments in the index samples determine where on the probe array hairpin ligators (and thus, fragments) become coupled. The presence of hairpin ligators at different locations in the probe arrays thus forms a pattern of signals that provides a signature or fingerprint of a nucleic acid sample based on the presence or absence of specific nucleic acid sequences in the sample. For this reason, cataloging of this pattern of signals (that is, the pattern of the presence of hairpin ligators) is an embodiment of the disclosed method that is of particular interest. Catalogs can be made up of, or be referred to, as, for example, a pattern of hairpin ligators on probe arrays, a pattern of the presence of hairpin ligators on probe arrays, a catalog of nucleic acid fragments in a sample, or a catalog of nucleic acid sequences in a sample. The information in the catalog is preferably in the form of positional information (that is, location in the probe array) or, more preferably, in the form of sequences. Preferred sequence information for catalogs include sequences of probe array probes to which a hairpin ligator was coupled and sequences of nucleic acid fragments present in the sample (derived from the locations in the probe array where hairpin ligators were coupled).

Such catalogs of nucleic acid samples can be compared to a similar catalog derived from any other sample to detect similarities and differences in the samples (which is indicative of similarities and differences in the nucleic acids in the samples). For example, a catalog of a first nucleic acid sample can be compared to a catalog of a sample from the same type of organism as the first nucleic acid sample, a sample from the same type of tissue as the first nucleic acid sample, a sample from the same organism as the first nucleic acid sample, a sample obtained from the same source but at a different time than the first nucleic acid sample, a sample from a different organism than the first nucleic acid sample, a sample from a different type of tissue than the first nucleic acid sample, or a sample from a different type of organism than the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, or the same cDNA, or the same cDNA library. Samples from the same source that are to be compared are preferably collected at different times (thus allowing for potential changes over time to be detected). This is especially useful when the effect of a treatment or change in condition is to be assessed. A different organism refers a different individual organism, such as a different patient, a different individual animal. Different organism includes a different organism of the same type or organisms of different types. A different type of organism refers to organisms of different types such as a dog and cat, a human and a mouse, or E. coli and Salmonella. A different type of tissue refers to tissues of different types such as liver and kidney, or skin and brain.

Detecting the presence of hairpin ligators on a probe array can be accomplished by detection of labels incorporated into, or coupled to, the hairpin ligators. Alternatively, the hairpin ligators can be detected based on detection of their sequence. Any of the numerous sequence-specific detection techniques can be used for this purpose, including, for example, hybridization of labeled probes. The loop sequence of the hairpin primer, for example, is a preferred site for binding of a detector tag by complementary hybridization. In this embodiment, the loop portion of the hairpin primer should be long enough to permit effective binding of a complementary nucleic acid. Design of hybridization probes and hybridization conditions are well known. Preferred probe lengths for this purpose are 12 to 20 bases. The nucleic acid tag may additionally bind to the bases in one side of the stem. The presence of hairpin ligators can also be detected by generating a signal mediated by the hairpin ligator, its associated fragment, or the second primer sequence at the other end of the fragment. Use of the second primer sequence as a primer for primer extension, described below, is a preferred example of this.

When coupling of a hairpin ligator to a detector probe involves the use of a strand having a 5' hairpin structure (top strand in FIG. 4), the coupling event links the strand to the detector probe via the 5' end of the hairpin ligator, which contains, for example, a 5'-phosphate capable of participating in ligation. After coupling, there remains a free 3'-terminus at the other end, which may be used for a labeling reaction. Where the strand has a 3' hairpin structure at this other end (as in the bottom strand in FIG. 5), the strand can be labeled by primer extension. Labeling is preferably performed using primer extension by the Klenow fragment of DNA polymerase I, in the presence of fluorescent dNTPs.

The signal to be detected for the nucleic acid fragments can be increased by nucleic acid amplification. It is preferred either that the nucleic acid fragments (including hairpin ligators) that have been coupled to the detector probes be amplified or mediate amplification of another nucleic acid. The fragments can be amplified using any suitable method. Preferred amplification methods are those that work efficiently for the generation of surface-localizable signals. A preferred method is branch DNA amplification (Urdea,

*Biotechnology* 12:926 (1994); Horn et al., *Nucleic Acids Res.* 25(23):4835–4841 (1997). A second preferred method is rolling circle amplification (PCT application WO 97/19193; Lizardi et al., *Nature Genetics* 19(3):225–232 (1998)). Other methods include polymerase chain reaction (PCR), ligase chain reaction (LCR), self-sustained sequence replication (3 SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics*, 9:199–202 (1993)). Amplification primers can be based, for example, on the sequence of the hairpin primers and second primers. It is preferred that amplification primers be based on hairpin primer sequences that appear in the loop of the hairpin structure. In this way, all of the fragments can be amplified using the same primer if the hairpin primers are designed to have the same loop sequence. In this case, the primer sequences and stem sequences of the hairpin primers can be different as discussed elsewhere herein.

Amplification of the fragment is facilitated by the presence of hairpin primer sequence at the end of the fragment (and by the presence of second primer sequence at the other end). For example, the primer sequences can be used for amplification primer sequences. The primer sequences can also be used to circularize the adaptor/fragments for subsequent amplification by rolling circle replication. Rolling circle amplification is described in U.S. Pat. No. 5,854,033 and PCT application WO 97/19193.

In one embodiment, hybridization of amplified fragments to detector probes can be aided by shortening the fragment length prior to hybridization. This can be accomplished, for example, by digesting the fragment with a restriction endonuclease. Preferably, the recognition site for the restriction endonuclease is included in the sequence of the hairpin primer. For this purpose, it is preferred that the restriction enzyme used has a cleavage site offset from the recognition site. The following example illustrates use of the non-palindromic Type III enzyme EcoP15I (New England Biolabs) to shorten the length of amplified fragments prior to hybridization. EcoP15I recognizes and cleaves the following site (SEQ ID NO:10):

5'-CAGCAGNNNNNNNNNNNNNNNNNNNNNNN N^NN-3'

3'-GTCGTCNNNNNNNNNNNNNNNNNNNNNNN NN^-5' where the carets (^)mark the cut sites in each strand. Amplification using a hairpin primer having the sequence (SEQ ID NO:11)

5'-<u>TCTAGTCC</u>AATCCAAGCTACATCAGCAGATGC <u>GGACTAGA</u>-3' results in the following double stranded fragment (SEQ ID NO:12; the recognition site is boldface, the stem sequences are underlined)

5' . . NNNNNNNNNNNGACCTGTCTAGTCCGCAT CTGCTGATGTAGCTTGGATT<u>GGACTAGA</u>-3'

3' . . NNNNNNNNNNNCTGGAC<u>AGATCAGG</u>CGT AGACGACTACATCGAACCTAACCTGATCT-5'

Digestion with EcoP15I will result in the cleaved fragment

5'-NNNNNNNNNGACCTG<u>TCTAGTCC</u>GCATCTGCT GATGTAGCTTGGATT<u>GGACTAGA</u>-3'

3'-NNNNNNNCTGGAC<u>AGATCAGG</u>CGTAGACGAC TACATCGAACCTAACCTGATCT-5'

The bottom strand can then form the hairpin structure (nucleotides 1–53 of SEQ ID NO:12)

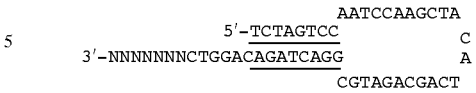

Coupling of this shortened fragment to a detector probe results in the structure (SEQ ID NO:21)

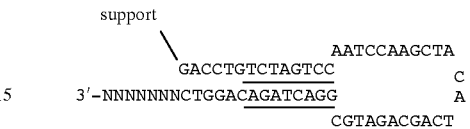

In another embodiment, the strands of amplified nucleic acid fragments can be separated prior to hybridization to the detector probes. Such strand separation can improve the efficiency of both formation of the hairpin structure and hybridization of the amplified fragment to the detector probe. This separation can be accomplished using any suitable technique. Strand separation is preferably accomplished by strand-specific digestion. This can be accomplished, for example, by digesting one of the strands with a nuclease such as T7 gene 6 exonuclease. By incorporating a few phosphorothioate linkages at the 5' end of the hairpin primer, the strand containing the hairpin primer will be protected from exonuclease digestion while the other strand is digested. Alternatively, the other (non-hairpin) primer can be made with 5' end phosphorothioate linkages. This will protect the opposite strand from digestion.

Strand separation can also be accomplished by including a capture tag on the hairpin primer or the second primer. Capture tags and their use are described above. A preferred capture tag is a biotin incorporated into a primer by using a biotin-T phosphoramidite (Glen Research No. 10-1038-95). This modified nucleotide does not interfere with primer function, and becomes incorporated into all newly-synthesized DNA strands during PCR amplification. If the strand to be captured is a strand with a 5' hairpin structure (top strand in FIG. 4), the biotin-T is present as part of the hairpin primer. On the other hand, if the strand to be captured is a strand with a 3' hairpin structure (bottom strand in FIG. 4), the biotin-T is present as part of the second primer. The preferred location of the biotin-T in the hairpin primer is any thymine base present in the loop sequence. Capture of the biotinylated strand may be performed by methods well known in the art, such as the use of streptavidin-magnetic particles (Dynal, Inc.). This capture tag can then be used to immobilize one strand of the amplified fragments while the other strands are washed away. Either the immobilized or washed strand can be carried forward in the method.

In another embodiment, the concentration of the various nucleic acid fragments in the index samples are normalized. Normalization can be preformed either before or after any amplification step that may be used. A preferred technique for fragment normalization involves immobilizing one strand of the nucleic acid fragments, denaturing the nucleic acid fragments, renaturing the nucleic acid fragments for a time greater than the $c_0 t_{1/2}$ for abundant nucleic acid fragments and less than the $c_0 t_{1/2}$ for rare nucleic acid fragments, and collecting the un-renatured nucleic acid fragments.

The sequence information that can be obtained with the disclosed method can be illustrated using a specific example of a nucleic acid fragment. Assume a nucleic acid sample containing a nucleic acid fragment with the sequence (SEQ ID NOs:13 and 14)

. . CGCACGGGCTATAGCTGATATAG . . GGCAAAT-
    GTCTAGTCCGAAATCCAAGCTATG . .
    . . GCGTGCCCGATCTCGACTATATC . . CCGTTTA-
    CAGATCAGGCTTTAGGTTCGATAC . .

If the sample is amplified with a hairpin primer having the sequence TCTAGTCCGAATGTAGCTTGGATT TCGGACTAGA (SEQ ID NO:15; where the primer sequence is in boldface and stem sequences are underlined) and a second primer having the sequence ACGGGCTATAGCTGATATAG, the following amplified fragment will result (SEQ ID NOs:16 and 17):

ACGGGCTATAGCTGATATAG. .GGCAAAT-
    GTCTAGTCCGAAATCCAAGCTACATTCG-
    GACTAGA
    TGCCCGATCTCGACTATATC. .CCGTTTAC
    AGATCAGGCTTTAGGTTCGATGTA
    AGCCTGATCT

When a hairpin structure is formed in the lower strand, the following nucleic acid is obtained (SEQ ID NOs:16 and 17).

```
                                            ATGTAG
                               TCTAGTCCGA        C
    TGCCCGATCTCGACTATATC..CCGTTTACAGATCAGGCT     T
                                            TTAGGT
```

When this nucleic acid is hybridized to an appropriate detector probe (a hexamer in this example) and the detector probe and hairpin ligator are coupled the following structure is obtained (SEQ ID NO:16 and SEQ ID NO:20).

```
                    support               ATGTAG
                         `CAAATGTCTAGTCCGA    C
    TGCCCGATCTCGACTATATC..CCGTTTACAGATCAGGCT  T
                                         TTAGGT
```

The sequence of the detector probe is identified by the location in the probe array where the hairpin ligator is detected. The sequence of the adjacent primer sequence is identified by the probe array in which the label of the hairpin ligator is detected (since a different set of probe arrays is used for each index sample).

Thus, in this example, detection of label in the CAAATG hexamer position of the TCTAGTCCGAAATCCAAGCT (nucleotides 9–28 of SEQ ID NO: 17) probe array (TCTAGTCCGAAATCCAAGCT (nucleotides 9–28 of SEQ ID NO: 17) corresponds to the primer sequence in the hairpin primer sequence in this example) indicates the presence of a nucleic acid fragment in the nucleic acid sample having the sequence CAAATGTCTAGTCCGAAATCCAAGCT (nucleotides 3–28 of SEQ ID NO: 14).

Hairpin primers may also be utilized to multiplex a one color readout of a control and tester fragments of a gene from the same address of a slide array. One way to do this is to use labile and stable forms of hairpin primers as described in the following illustration.

1. Generate PCR products from cDNA using adaptor ligation. Use different hairpin primers for the tester and control, a uracil in the synthetic adapters for the testers and a thymine in the synthetic adapters for the controls. A fluorescence label my be incorporated into the hairpin using standard fluorescent labeled nucleotides.

2. Hybridize and ligate to probe array

```
    xxxxxxNNNNNNNNNNNNNNN
    |||||||||||||||||||  dT  (Stable Hairpin, Control)
    ...nnnnnnnnnnNNNNNNNNNN*NN
    xxxxxxNNNNNNNNNNNNNNN
    |||||||||||||||||||  U   (Labile Hairpin, Tester)
    ...nnnnnnnnnnNNNNNNNNNN*NN
``` where x is the hexamer probe, N is the hairpin, n is the amplified fragment, | indicates base pairing, * indicates a fluorescently labeled nucleotide.

3. Read the fluorescence signal at a hexamer probe location. This corresponds to the control plus tester fluorescence.

4. Treat the probe array with uracil-DNA glycosylase. This will cleave hairpins containing uracil at the uracil and leave the thymine uncleaved.

5. Wash the slide with alkali to remove the cleaved fragments.

6. Read the fluorescence signal from the hexamer probe location. This signal corresponds only to the control sample.

7. The tester/control ratio is calculated from the signals of steps 3 and 6. Ratio=(signal$_3$–signal$_6$)/signal$_6$.

Another mode for the use of a uracil containing hairpin is as follows.

1. Generate PCR products from CDNA using adaptor ligation. Use different hairpin primers for the tester and control, a uracil in the synthetic adapters for the testers and a thymine in the synthetic adapters for the controls.

```
    xxxxxxNNNNNNNNNNNNNNN
    |||||||||||||||||||  U   Labile Hairpin (control)
    ...nnnnnnnnnnNNNNNNNNNN
    xxxxxxNNNNNNNNNNNNNNN
    |||||||||||||||||||  U   Labile Hairpin (tester)
    ...nnnnnnnnnnNNNNNNNNNNM
``` where x is the hexamer probe, N is the hairpin, M is an additional base or bases, n is the binary sequence tag, | indicates base pairing.

2. Hybridize and ligate to probe array.

3. Wash with alkali to remove non-ligated tag-hairpins.

4. Cleave with uracil-DNA glycosylase.

The released fragment to be analyzed will be:

. . . nnnnnnnnnnNNNNNNNNNNN (control)
   . . . nnnnnnnnnnNNNNNNNNNNM (tester)

5. Detect the cleaved tags, resolving the two different masses, using MALDI-TOF. Use of a tandem mass spectrometer to fragment the cleaved tags will determine some or all of the tag sequence, and improve the signal to noise.

A preferred form of the disclosed method involves amplification of nucleic acid fragments to which adaptor-indexers have been coupled. An example of this form of the method is illustrated in FIG. 6. Coupling of adaptor-indexers to nucleic acid fragments involves the following basic steps. A nucleic acid sample, embodied in double stranded DNA, is digested with one or more restriction endonucleases such that a set of DNA fragments having sticky ends with a variety of sequences is generated. Preferred for this purpose is the use of a single Type IIS restriction endonuclease having an offset cleavage site. Since such Type IIS restriction endonucleases cleave at a site different from the recognition sequence, this results in a set of DNA fragments having sticky ends with a variety of sequences. A similar effect can be obtained by digesting the nucleic acid sample with a mixture of restriction endonucleases which cleave at their recognition site.

For a four base sticky end, there are 256 possible sequences. The general formula is $N=4^X$ where X is the length of the sticky end and N is the number of possible sequences. In a sufficiently complex nucleic acid sample, all of these sequences will be represented in the ends of the set of DNA fragments. The nucleic acid sample is also divided into aliquots (referred to as index samples); preferably as many aliquots as there are sticky end sequences (for example, $N=4^X$ aliquots). Where multiple restriction endonucleases are used, the nucleic acid sample is preferably divided into index samples before digestion. Where a single restriction endonuclease is used, the nucleic acid sample is preferably divided into index samples following digestion. Each index sample is then mixed with a different adaptor-indexer, each of which has a sticky end compatible with one of the possible sticky ends on the DNA fragments in that index sample. The adaptor-indexes are then coupled onto compatible DNA fragments.

Each index sample can then be digested with one or more other restriction enzymes (referred to as second restriction enzymes), preferably restriction enzymes having a four base recognition sequences. All index samples are preferably digested with the same restriction enzyme(s). Alternatively, the index samples can be further divided into secondary index samples with each digested with a different second restriction enzyme or set of restriction enzymes. A second adaptor can then be coupled to the DNA fragments in the index samples (or secondary index samples). Preferably, the same second adaptor is used for each index sample. Different second adaptors are preferably used with secondary index sample derived from the same index sample. In this case, it is preferred that the same set of second adaptors be used with each set of secondary index samples. DNA fragments in each index sample (or secondary index sample) now have adaptors coupled to each end. The DNA fragments can then be amplified using hairpin primers. Sequences in the adaptors can be used as primer binding sites for this amplification.

Optionally, prior to amplification, the index samples (or secondary index samples) can divided into further aliquots. These are referred to as restricted index samples and non-restricted index samples (or restricted secondary index samples and non-restricted secondary index samples, if there are secondary index samples). Generally, the index samples (or secondary index samples) can be divided into one or more restricted index samples and one non-restricted index sample. The restricted index samples (or restricted secondary index samples), but not the non-restricted index sample (or non-restricted secondary index sample) are then each digested with a different restriction endonuclease (referred to as third restriction enzymes). The third restriction enzymes are preferably different from any of the restriction enzymes or second restriction enzymes with which the sample has been digested.

In some cases, the third restriction enzymes will cleave some DNA fragments in the restricted index samples (or restricted secondary index samples), thus making the fragment incompetent for amplification. In this way, the signals generated by the restricted index samples and non-restricted index sample (or restricted and non-restricted secondary index samples) can differ, and fragments containing the recognition sequence of one of the third restriction enzymes can be identified.

Secondary index samples, restricted index samples, non-restricted index samples, restricted secondary index samples, and non-restricted secondary index samples are referred to collectively herein as derivative index samples. Each is derived from an index sample and, in some cases, from another derivative index sample. In general, only those derivative index samples last generated are carried forward in the method. For example, if secondary index samples are created, the original index samples from which they were derived are no longer carried forward in the method (the secondary index samples are). Similarly, if restricted and non-restricted secondary index samples are created, then neither the original index samples nor the secondary index samples from which the restricted and non-restricted secondary index samples were derived are carried forward in the method. However, additional information may be gained by carrying forward all or some of the index samples and derivative index samples.

Each processed DNA fragment (that is, each DNA fragment to which an adaptor-indexer was coupled) from the sample will result in a signal at a particular location in a particular array of detector probes. In preferred embodiments, the probe array in which the signal for a given fragment is detected is determined by the sequence of the original sticky end sequence (or recognition sequence). Each different sticky end or recognition sequence is processed in a separate index sample; a separate probe array is used for each index sample or derivative index sample. The location in the probe array in which the signal for a given fragment is detected is determined by the sequence in the DNA fragment adjacent to the stem of the hairpin structure, which is preferably the sequence adjacent to the sticky end sequence (or recognition sequence), since the detector probe must hybridize to this sequence in order to be coupled to the hairpin ligator on the fragment. Hybridization based on the sequence adjacent to the sticky end sequence (or recognition sequence) is accomplished by designing the hairpin primer to result in formation of a hairpin structure with a stem that includes, and terminates at, the sticky end sequence (see example below). A complex nucleic acid sample will produce a unique pattern of signals on the probe arrays. It is this pattern that allows unique cataloging of nucleic acid samples and sensitive and powerful comparisons of the patterns of signals produced from different nucleic acid samples.

The probe array, and location in the probe array, where a DNA fragment generates a signal identifies the sequence of the sticky end of the DNA fragment and of the sequence adjacent to the sticky end (or the recognition sequence of the restriction enzyme and of the sequence adjacent to the recognition sequence). This is a ten base sequence when a four base sticky end and six base detector probes are used. The fixed relationship between the recognition sequence and the cleavage site of a Type IIS restriction enzyme, when used, and the identity of the recognition sequence, provide additional sequence information about the DNA fragment.

This form of the disclosed method is performed using one or more restriction enzymes that collectively produce a plurality of different sticky end sequences. Preferably, the sticky end sequences generated by the restriction enzyme are not limited by the recognition sequence of the restriction enzyme. The sticky ends generated are preferably 2, 3, 4 or 5 nucleotides long. Preferred restriction enzymes for use in the disclosed method are Type IIS restriction endonucleases, which are enzymes that cleave DNA at locations outside of (or offset from) the recognition site and which generate sticky ends. Examples of Type IIS restriction endonucleases are FokI, BbvI, HgaI, BspMI and SfaNI.

Restriction endonucleases for use in this embodiment of the disclosed method produce sticky ends encompassing permutations and combinations of the four nucleotides, A, C, G, and T. The larger the number of protruding bases, the greater the number of possible permutations and combinations of terminal nucleotide sequences, and the more specific the indexing is likely to be. For example, a restriction endonuclease such as FokI, which releases fragments with four base, 5'-protruding sticky ends, will generate fragments having $4^4$ or 256 possible protruding tetranucleotide ends. Cleavage of a CDNA sample having an average of 12,000 different cDNAs with the restriction endonuclease FokI will produce a mixture of fragments with four base, 5'-protruding ends. On average, FokI cuts twice in every $4^5$ base pairs giving an average fragment size of 512 base pairs. If the average length of cDNA is 1,700 base pairs, each cDNA will produce approximately four fragments. The entire sample will contain approximately 4*12,000=48,000 fragments. There are $4^4$=256 possible tetranucleotide sequences and therefore 256 possible identities for each sticky end. On average, there will be 48,000/256=188 fragments with a given sticky end sequence. Each of these fragments is sorted by hybridization to different detector probes based on the sequence adjacent to the sticky end sequence in each fragment. A hexamer probe array has 4,096 different six nucleotide probes. Thus, only 188 of the 4,096 hexamers in the probe array will couple to a hairpin ligator, on average. With 256 probe arrays each having 4,096 different hexamer probes, there are 256*4,096=1,048,576 "bins" in which to distribute 48,000 fragments. This leaves ample opportunity to identify different patterns when using different cDNA samples.

Cleavage of human genomic DNA (which has a haploid number of $3 \times 10^9$ base pairs) with the restriction endonuclease Bsp24I will release a large and complex mixture of fragments with five base, 3'-protruding ends. On average, Bsp24I cuts twice in every 46 base pairs giving an average fragment size of 2048 base pairs, and resulting in $3 \times 10^9/2048$ approximately $1.5 \times 10^6$ fragments. There are $4^5$=1024 possible pentanucleotide sequences and therefore 1024 possible identities for each sticky end. On average, there will be $1.5 \times 10^6/1024$=1,465 fragments with a given sticky end sequence. Each of these fragments is sorted by hybridization to different detector probes based on the sequence adjacent to the sticky end sequence in each fragment. An heptamer probe array has 16,384 different seven nucleotide probes. Thus, only 1,465 of the 16,384 heptamers in the probe array will couple to a hairpin ligator, on average. With 1024 probe arrays each having 16,384 different heptamer probes, there are 1024*16,384=$1.6 \times 10^7$ "bins" in which to distribute $1.5 \times 10^6$ fragments.

Cleavage of a cDNA sample with twenty different restriction endonucleases having six-base recognition sequences will produce a mixture of fragments with sticky ends. On average, restriction endonucleases having six-base recognition sequences cut once every $4^6$=4096 base pairs. If the sample contains approximately 12,000 cDNA molecules with an average length of CDNA is 1,500 base pairs, cleavage with one of the restriction enzymes will result about 3200 cuts (and thus 6400 DNA fragments with sticky ends). Further cleavage of the sample (second digest) with two different restriction endonucleases having four-base recognition sequences will result in additional cuts once every $4^4$=256 base pairs. Since the second digest will, in many cases, result in cuts on each fragment, this will result in (for each of the 20*2=40 secondary index samples) approximately 6,400 fragments, each approximately 256 base pairs long.

If five different restriction endonucleases having four-base recognition sequences are used for the third digest, approximately half of the fragments in each restricted secondary index sample will be cleaved (since these restriction enzymes will cut about once every 256 base pairs). Thus, there will be approximately 3,200 fragments (intact, with both an adaptor-indexer and a second adaptor) in each of the 20*2*5=200 restricted secondary index samples (there will be approximately 6,400 fragments in the non-restricted secondary index sample). Each of these fragments is sorted by hybridization to different detector probes based on the sequence adjacent to the sticky end sequence in each fragment. A hexamer probe array has 4,096 different six nucleotide probes. Thus, only 3,200 of the 4,096 hexamers in the probe array will couple to a hairpin ligator, on average. With 200 probe arrays each having 4,096 different hexamer probes, there are 200*4,096=819,200 "bins" in which to distribute the of 3,200*200=640,000 total fragments (a heptamer array would provide 200*16,384=3,276,800 "bins").

As these examples illustrate, the length of the recognition sequence, the length of the sticky end generated, and the length of the detector probes used in the probe arrays together determine the number of data bins into which the nucleic acid fragments are sorted. By using sticky ends and array probes of sufficient length, the sorting of fragments can be matched to the complexity of the sample being analyzed.

The use of a comprehensive panel of adaptor-indexers provides a means for attaching specific functional modifications to selected subsets of a complex mixture of nucleic acid fragments and identifying the molecules so modified. Such a defined subset of molecules may be further resolved by additional cleavage and indexing, or by any of the established techniques such as cloning, PCR amplification, or gel electrophoresis. Individual members of the class may be distinguished by identifying characteristics such as length, sequence, or restriction endonuclease maps. The sequence of the sticky ends of the adaptor-indexers provides a means of indexing a large number of nucleic acid fragments.

Detector probes of different sequence can be immobilized at different locations on the probe array. In this way, the sequence of the detector probes on the probe array and the sequence of nucleic acid fragments in the index samples determine where on the probe array amplified fragments become coupled. The presence of fragments at different locations in the probe arrays thus forms a pattern of signals that provides a signature or fingerprint of a nucleic acid sample based on the presence or absence of specific nucleic acid sequences in the sample. For this reason, cataloging of this pattern of signals (that is, the pattern of the presence of fragments or hairpin ligators) is an embodiment of the disclosed method that is of particular interest. Catalogs can be made up of, or be referred to, as, for example, a pattern of fragments on probe arrays, a pattern of the presence of fragments on probe arrays, a pattern of hairpin ligators on probe arrays, a pattern of the presence of hairpin ligators on probe arrays, a catalog of nucleic acid fragments in a sample, or a catalog of nucleic acid sequences in a sample. The information in the catalog is preferably in the form of positional information (that is, location in the probe array) or, more preferably, in the form of sequences. Preferred sequence information for catalogs include sequences of detector probes to which a fragment was coupled and sequences of nucleic acid fragments present in the sample (derived from the locations in the probe array where fragments were coupled).

When a single Type IIS restriction enzyme is used in the first digest, the sequence information obtainable can be illustrated with the following structures:

DNA fragment: . . NNNNXXXX . . NNNNRRRR-ROOOOOOOOOSSSSNNNN . .

Sequence information: RRRRROOOIIIIISSSS

In these structures, each character represents a nucleotide. N represents any nucleotide (having no special identity or relationship to the method). R represents a nucleotide in the recognition sequence of the Type IIS restriction enzyme. O represents a nucleotide in the offset between the recognition site and the cleavage site of the Type IIS restriction enzyme. S represents a nucleotide in the sticky end resulting from cleavage with the Type IIS restriction enzyme. X represents a nucleotide in the recognition/cleavage site of the second restriction enzyme. I represents a nucleotide complementary to the detector probe.

From the DNA fragment . . . NNNNXXXX . . . NNNNR-RRRROOOOOO OOOSSSSNNNN . . . , the sequence information RRRRROOOIIIIISSSS can be obtained. In this example, the Type IIS restriction enzyme has a five base recognition sequence, a nine base offset to the cleavage site, and creates a four base sticky end. The detector probes contain hexamer sequences. Each array location where a signal is generated in this example thus represents a specific sequence: nnnnn - - - nnnnnnnnn (where n represents an identified nucleotide and each—represents an unidentified nucleotide). This is referred to as a determined sequence. The portion of the nucleic acid fragments for which the sequence is determined corresponds to the sticky end sequence, the sequence adjacent to the sticky end sequence to which the detector probe hybridized, and the recognition sequence of the restriction enzyme (S, I, and R, respectively).

This sequence information can also be represented by the structure

A-B-C-D where A is the recognition sequence of the restriction enzyme, B is the gap of unknown sequence, C is the sequence to which the detector probe hybridized, and D is the sticky end sequence. The gap represents the nucleotides between the recognition sequence and the sequence to which the detector probe hybridized. C is always adjacent to the sticky end sequence D. In the example above, A is RRRRR, B is OOO, C is IIIIII, and D is SSSS.

The sequence information that can be obtained with the disclosed method can be further illustrated using a specific example of a nucleic acid fragment. Assume a nucleic acid sample containing a nucleic acid fragment with the sequence (SEQ ID NO: 18)

. . CGGTGGATGACTTGAAGCTATGCTTAGG . .
. . GCCACCTACTGAACTTCGATACGAATCC . .

If the sample is digested with FokI—a Type IIS restriction enzyme with a recognition sequence of GGATG and a cleavage site offset by 9 and 13 nucleotides—the fragment will be cleaved to generate the following fragments (the FokI recognition sequence is shown in bold)

. . CGGTGGATGACTTGAAGC TATGCTTAGG . .
. . GCCACCTACTGAACTTCGATAC GAATCC . .

When the corresponding adaptor-indexer is coupled to fragment and the coupled fragment is amplified using a corresponding hairpin primer, the following nucleic acid is obtained (SEQ ID NO: 19; sequence from the adaptor-indexer is underlined, the hairpin primer is italicized)

. . CGGTGGATGACTTGAAGCTATGCGGTAT-TACAGCCTATATACCGCATA

. . GCCACCTACTGAACTTCGATAC GCCATAATGTCGGATATATGGCGTAT

When the hairpin structure is formed (in the bottom strand in this example), the nucleic acid is hybridized to an appropriate detector probe (a hexamer in this example), and the detector probe and hairpin ligator are coupled the following structure is obtained (SEQ ID NO:22)

```
        support                    ATAG
           `TGAAGCTATGCGGTAT       G
    ..GCCACCTACTGAACTTCGATACGCCATA  C
                                   ATGT
```

The sequence of the detector probe is identified by the location in the probe array where the fragment is detected. The sequence of the adjacent sticky end is identified by the probe array in which the fragment is detected (since a different probe array is used for each sticky end sequence). Finally, the sequence of the recognition sequence is identified by the relationship of the cleavage site to the recognition sequence. Thus, in this example, detection of label in the TGAAGC hexamer position of the ATAC sticky end probe array indicates the presence of a nucleic acid fragment in the nucleic acid sample having the sequence CCTACNNNACTTCGATAC (3' to 5'; SEQ ID NO:23).

Relating this sequence to the generalized structure A-B-C-D, A is CCTAC, B is NNN, C is ACTTCG, and D is ATAC.

When multiple restriction enzymes are used for the first digestion, the sequence information obtainable can be illustrated with the following structures:

DNA fragment: . . NNXXXXXNN . . NNRRRRNN . . NNIIIIIISSSSSSNN . .

Sequence: XXXX . . . . . . RRRR . . . . . . IIIIIISSSSSS

In these structures, each character represents a nucleotide. N represents any nucleotide (having no special identity or relationship to the method). S represents a nucleotide in the recognition sequence (including sticky end) of the first restriction enzyme. X represents a nucleotide in the recognition/cleavage site of the second restriction enzyme. R represents a nucleotide in the recognition sequence of the third restriction enzyme. I represents a nucleotide complementary to the detector probe. The sequence and distance between the recognition sites of the second and third restriction enzymes and between the recognition site of the second restriction enzyme and the probe complement are not determined in the basic method.

From the DNA fragment . . . NNXXXX. . . . .NNIIIIII SSSSSSNN. . . , the sequence information XXXX. . . RRRR. . .IIIIIISSSSSS can be obtained. In this example, the detector probes contain hexamer sequences. Each array location where a signal is generated in this example thus represents a specific sequence: nnnn. . . .nnnn. . .nnnnnnnnnnnn (where n represents an identified nucleotide and each . . . represents an unidentified gap sequence). This is referred to as a determined sequence. The portion of the nucleic acid fragments for which the sequence is determined corresponds to the recognition sequence of the first restriction enzyme, the sequence adjacent to the recognition sequence to which the detector probe hybridized, the recognition sequence of the second restriction enzyme, and the recognition sequence of the third restriction enzyme (S, I, X, and R, respectively).

This sequence information can also be represented by the structure

E-B-F-B-C-D where B is a gap of unknown sequence, C is the sequence to which the detector probe hybridized, D is the recognition sequence of the first restriction enzyme, E is the recognition sequence of the second restriction enzyme, and F is the recognition sequence of the third restriction enzyme. The gaps represent nucleotides between the recognition sequences of the second and third restriction enzymes and between the recognition sequence of the third restriction enzyme and the sequence to which the detector probe hybridized. C is always adjacent to the recognition sequence D. In the example above, C is IIIIII, D is SSSSSS, E is XXXX, and F is RRRR.

The sequence information that can be obtained with the disclosed method can be further illustrated using a specific example of a nucleic acid fragment. Assume a nucleic acid sample containing a nucleic acid fragment with the sequence (SEQ ID NOs:24, 25, and 26; restriction enzyme recognition sequences in boldface)

..CGCATGGG..ATAGCTTG..CAAGCTATGGATC-CGA..

..GCGTACCC..TATCGAAC..GTTCGATACCTAG-GCT..

If the sample is first digested with BamHI - - a restriction enzyme with a recognition sequence of GGATCC generating a four-base sticky end - - the fragment will be cleaved to generate the following fragments:

. . CGCATGGG . . ATAGCTTG . . CAAGCTATG GATCCA ..

.. GCGTACCC .. TATCGAAC .. GTTCGATACCTAG GT . .

When the corresponding adaptor-indexer is coupled to fragment and the fragment digested with NlaI (recognition sequence CATG) the result is (SEQ ID NO:27):

.. CGCATG GG .. ATAGCTTG .. CAAGCTATG-GATCTGGTATTACAGCCTA

.. GC GTACCC .. TATCGAAC .. GTTCGATACCTA-GACCATAATGTCGGAT

After addition of the second adaptor and amplification using the corresponding hairpin primer (GGATCTGGTATAGGCTGTAATACCAGATCC; SEQ ID NO:28), the following nucleic acid is obtained (SEQ ID NO: 33 and SEQ ID NO:29; sequence from the adaptor-indexer is underlined, the hairpin primer is italicized). Note that the hairpin primer hybridizes to both the sticky end sequence and the remaining recognition sequence (that is, the C not in the sticky end).

GCCATGGATCTCTCACATGGG . . ATAGCTTG . .

CGGTACCTAGAGAGTGTACCC . . TATCGAAC . .

. . CAAGCTATGGATCTGGTATTACAGC-CTATACCAGATCC

. . GTTCGATACCTAG<u>ACCATAATGTCGGA</u>TATG-GTCTAGG

An aliquot (that is, a restricted index sample) of the sample can be digested with AluI (recognition site AGCT) prior to amplification. By cutting the fragment, amplification is prevented. This lack of amplification in the restricted index sample indicates the presence of the sequence TCGA in the fragment.

When a hairpin structure is formed in the bottom strand (in this example), the fragment is hybridized to an appropriate detector probe (a hexamer in this example), and the detector probe and hairpin ligator are coupled the following structure is obtained (SEQ ID NO:30; sequence from the adaptor-indexer is underlined, the hairpin primer is italicized, restriction enzyme recognition sequences in boldface)

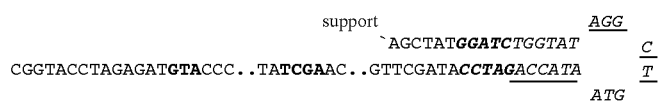

The sequence of the detector probe is identified by the location in the probe array where the hairpin ligator is detected. The sequence of the adjacent recognition sequence (including the sticky end) is identified by the probe array in which the hairpin ligator is detected (since a different set of probe arrays is used for each index sample). The sequence of the recognition sequence of the second restriction enzyme is identified by the probe array in which the hairpin ligator is detected (since a different set of probe arrays is used for each secondary index sample). Finally, the presence of an internal sequence (the recognition sequence of the third restriction enzyme) is determined by seeing if the signal is absent from the probe array for the restricted secondary index sample that was digested with the third restriction enzyme (a different probe array is used for each restricted and non-restricted secondary index sample). If the signal is absent, it indicates the recognition site is present in the fragment.

Thus, in this example, detection of hairpin ligator in the AGCTAT hexamer position of the TCGA third recognition site probe array in the GTAC second recognition site set of probe arrays in the CCTAGG sticky end set of probe arrays indicates the presence of a nucleic acid fragment in the nucleic acid sample having the sequence

GTAC . . . TCGA . . . TCGATACCTAGG (SEQ ID NO:31).

Relating this sequence to the generalized structure E-B-F-B-C-D, C is TCGATA, D is CCTAGG, E is GTAC, and F is TCGA.

In another embodiment, the primer sequences in the hairpin primers are partly degenerate. In this way, multiple different nucleic acid fragments will be amplified in each index sample. Where partially degenerate primer sequences are used, it is preferred that the 3' end of the primer sequence of all of the hairpin primers used in a given index sample be the same. It is also preferred that the corresponding 3' end sequences of hairpin primers used in different index samples be different. In this way, the fragments amplified in each index sample will have related primer complement sequences while the sets of fragments amplified in the different index samples will be different. Such relationships provide a maximum of both sequence information for the fragments and catalog complexity.

The use of sets of hairpin primers with partially degenerate primer sequences can be illustrated with the following example. Sets of hairpin primers where the primers sequences in each set has, from 5' to 3', 8 specific bases and 12 degenerate bases can prime amplification from all sites in a nucleic acid sample having a sequence complementary to the 8 specified bases. The sequence of the specified bases in each of the sets can be different. Each different sequence, and thus each different set, of hairpin primers will prime amplification from a different set of sites in a nucleic acid sample. In a sufficiently complex nucleic acid sample, all of these sequences will be represented in the set of amplified fragments. By dividing the nucleic acid sample into aliquots (referred to as index samples) prior to amplification, multiple sets of fragments can be generated and analyzed, with each set preserving the primer sequence information.

Mass Spectroscopy Detection

Mass spectrometry techniques can be utilized for detection in the disclosed method. These techniques include matrix-assisted laser desorption/ionization time-of-flight (MALDI-TOF) mass spectroscopy. Such techniques allow automation and rapid throughput of multiple samples and assays.

Mass spectrometry detection works better with smaller molecules so it is useful to cut some components of the method prior to, or as part of mass spectrometry detection. A number of methods are contemplated where an oligonucleotide molecule to be detected is cut to a shorter length prior to detection by mass spectrometry. The disclosed method would proceed as normal and, in the preferred embodiment, the surface that has the detector probes attached would be compatible with the source region of a matrix assisted laser desorption ionization, time of flight, mass spectrometer (MALDI-TOF-MS). The resultant fragment would look something like

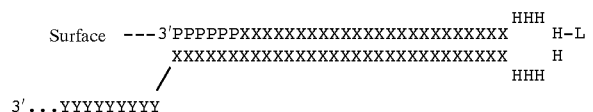

Where:

P are the detector probe, coupled to the fragment;

X are complementary bases of the hairpin primer and amplified fragment;

H are loop bases;

Y are the remaining nucleotides of the amplified fragment;

L is a label.

For fragments of greater than approximately 50 bases the performance of mass spectrometry techniques degrades for DNA samples. Chemical, biological, physical (thermal), and other cleaving reagents can be used to generate smaller, more optimal, sub-fragments to be analyzed in the mass spectrometer. The degree of fragmentation is somewhat tunable in instruments like the Q-TOF systems (Micromass, U.S. head office at Suite 407N, 100 Cummings Center, Beverly, Mass. 01915-6101, USA.) where one can look at the parent ion, then increase the fragmentation to see the decomposition fragments and thus the sequence; such a technique is contemplated to determine the fall sized sub-fragment, and infer the sequence of the sub-fragment through these known tools. The detectable fragment can be top strand, bottom strand, or both strands depending upon the scheme. The label may be a cleavable mass tag or the strand need not be labeled.

There are several useful cleaving reagents for this purpose. For example, one technique is that of Szybalski (described elsewhere herein) where FokI is used to cut at a fixed distance from an arbitrary, specific, recognition site. This technique can be extended to other restriction enzymes of Type IIS or Type III. One could also use this technique twice, once to trim off the end nearer the surface, once to trim off the end further from the surface; preferably one would use a Type II enzyme to cut the end furthest from the surface.

Use of McrBC (New England Biolabs), can be used to cut at methylcytosine sites adjacent to G/A. The cut site is not well defined (approximately 30 bases) which may be used to advantage to generate the parent as well as the fragmentation set. Metal containing porphyrins attached to oligonucleotides have been shown to cut DNA very near the porphyrin when exposed to light (texaphyrins, U.S. Pat. No. 5,607, 924). One could denature and use a hybridization texaphryin and light to cleave the remaining strand. Another cleavage technology is that of Dervan (Cartwright et al., Cleavage of chromatin with methidiumpropyl-EDTA. iron(II). Proc Natl Acad Sci U S A, 80(11):3213–7 (1983); Schultz, P. G. and P. B. Dervan, Sequence-specific double-strand cleavage of DNA by penta-N-methylpyrrolecarboxamide-EDTA XFe (II). Proc Natl Acad Sci U S A, 80(22):6834–7 (1983)). Techniques using photocleave linkages are described by Olejnik et al. (Olejnik et al., Photocleavable peptide-DNA conjugates: synthesis and applications to DNA analysis using MALDI-MS. Nucleic Acids Res, 1999. 27(23) :4626–31 (1999); Olejnik et al., Photocleavable affinity tags for isolation and detection of biomolecules. Methods Enzymol, 291:135–54 (1998); Olejnik et al., Photocleavable aminotag phosphoramidites for 5'-termini DNA/RNA labeling. Nucleic Acids Res, 26(15):3572–6 (1998); Olejnik et al., Photocleavable aminotag phosphoramidites for 5'-termini DNA/RNA labeling. Nucleic Acids Res, 26(15): 3572–6 (1998); Olejnik et al., Photocleavable biotin derivatives: a versatile approach for the isolation of biomolecules. Proc Natl Acad Sci U S A, 92(16):7590–4 (1995)) These linkages can be cleaved using light to release the fragment from the surface, thus allowing one to provide a more gentle desorption. WO 0004036 describes photocleavable nucleotides and methods for their use.

In one embodiment, a mass label such as peptide nucleic acid (PNA) molecules (Hanvey et al., Science 258:1481–1485 (1992)) of different sequence and molecular weight can be used as labels that bind specifically to sequence in hairpin primers or second primers. Laser desorption of the samples is used to generate MALDI-TOF mass spectra of the PNA labels, which are released into the spectrometer and resolved by mass. The intensity of each PNA label reveals the relative amount of different components. In other words, the PNA spectra generate scalar values that are indirect indicators of the relative abundance of the labeled component at specific locations in an array.

Multiplex detection using mass spectrometry can also be accomplished using sets of mass tags. The mass tags preferably have two key features. First, the tags are used in sets where all the tags in the set have similar properties. The similar properties allow the tags to be separated from other molecules lacking one or more of the properties. Preferably, the tags in a set have the same mass-to-charge ratio (m/z). That is, the tags in a set are isobaric. This allows the tags to be separated precisely from other molecules based on mass-to-charge ratio. The result of the filtering is a huge increase in the signal to noise ratio (s/n) for the system, allowing more sensitive and accurate detection.

Second, all the mass tags in a set can be fragmented, decomposed, reacted, derivatized, or otherwise modified to distinguish the different tags in the set. Preferably, the mass tags are fragmented to yield fragments of similar charge but different mass. This allows each mass tag in a set to be distinguished by the different mass-to-charge rations of the fragments of the tags. This is possible since, although the unfragmented mass tags in a set are isobaric, the fragments of the different mass tags are not.

Differential distribution of mass in the fragments of the mass tags can be accomplished in a number of ways. For example, mass tags of the same nominal structure (for example, peptides having the same amino acid sequence), can be made with different distributions of heavy isotopes, such as deuterium. All mass tags in the set would have the same number of a given heavy isotope, but the distribution of these would differ for different mass tags. Similarly, mass tags of the same general structure (for example, peptides having the same amino acid sequence), can be made with different distributions of modifications, such as methylation, phosphorylation, sulphation, and use of seleno-methionine for methionine. All mass tags in the set would have the same number of a given modification, but the distribution of these would differ for different mass tags. Mass tags of the same nominal composition (for example, made up of the same amino acids), can be made with different ordering of the subunits or components of the signal. All mass tags in the set would have the same number of subunits or components, but the distribution of these would be different for different mass tags. Mass tags having the same nominal composition (for example, made up of the same amino acids), can be made with a labile or scissile bond at a different location in the signal. All mass tags in the set would have the same number and order of subunits or components. Where the labile bond is present between particular subunits or components, the order of subunits or components in the mass tag can be the same except for the subunits or components creating the labile bond. Each of these modes can be combined with one or more of the other modes to produce differential distribution of mass in the fragments of the mass tags. For example, different distributions of heavy isotopes can be used in mass tags where a labile bond is placed in different locations.

The mass tags are preferably detected using mass spectrometry which allows sensitive distinctions between molecules based on their mass-to-charge ratios. The disclosed mass tags can be used as labels for any of the component of the disclosed method. For example, mass labels can be used on detector probes, adaptor-indexers, or hairpin primers. Preferably, the mass tags would be dissociated from the labeled component during, or prior to, detection. A set of isobaric mass tags can be used for multiplex labeling and/or detection of many amplified fragments since the mass tag fragments can be designed to have a large range of masses, with each mass individually distinguishable upon detection.

A preferred form of mass tag detection involves filtering of isobaric mass tags from other molecules based on mass-to-charge ratio, fragmentation of the mass tags to produce fragments having different masses, and detection of the different fragments based on their mass-to-charge ratios. The technique is best carried out using a tandem mass spectrometer where the isobaric mass tags are passed through a filtering quadrupole, the mass tags are fragmented in a collisional cell, and the fragments are distinguished and detected in a time-of-flight (TOF) stage. In such an instrument the sample is ionized in the source (for example, in a MALDI) to produce charged ions. It is preferred that the ionization conditions are such that primarily a singly charged parent ion is produced. A first quadrupole, Q0, is operated in radio frequency (RF) mode only and acts as an ion guide for all charged particles. The second quadrupole, Q1, is operated in RF+DC mode to pass only a narrow range of mass-to-charge ratios (that includes the mass-to-charge ratio of the mass tags). This quadrupole selects the mass-to-charge ratio of interest. Quadrupole Q2, surrounded by a collision cell, is operated in RF only mode and acts as ion guide. The collision cell surrounding Q2 will be filled to appropriate pressure with a gas to fracture the input ions by collisionally induced dissociation. The collision gas preferably is chemically inert, but reactive gases can also be used. Preferred molecular systems utilize mass tags that contain scissile bonds, labile bonds, or combinations, such that these bonds will be preferentially fractured in the Q2 collision cell.

Probability Detection

Sequencing by hybridization is known to produce mismatch errors (Lipshutz, Likelihood DNA sequencing by hybridization. J Biomol Struct Dyn, 11(3):637–53 (1993)). Database searching for sequence information currently is regular expression based and requires matched "letters" between the database entry and the search sequence. The disclosed method allows replacement of regular expression matching (match versus no-match per base) with a probability function to determine a confidence in the assignment of the identity of a sequence tag (that is, the fragments produced in the disclosed method).

The disclosed method uses covalent coupling to improve the specificity of the hybridization near the coupling site. Despite this improvement, there will remain a finite probability of a mismatch, particularly for nucleotides more removed from the coupling site. The error rate depends on least two mismatch properties:

base pairing, i.e. A with G;

distance from the coupling site.

As an illustration of the process to determine the confidence value, consider the two bases in a hexamer probe furthest from the coupling site, numbering the bases as shown here.

```
                          <hexamer>
    surface-linker-spacer-NNNNNNnnnn-hairpin ligator
                          ||||||||||||||||||||||||
              3'-fragment..NNNNNNNNNnnnn-hairpin ligator
                          123456 <position>
``` where for this particular case one has, surface - - - linker-spacer - - - ATXXXX, focusing on the AT (positions 1 and 2) bases for purpose of the immediate illustration.

To evaluate the possible set of sequences represented, weight matrices are used, following Dayhoff (Dayhoff et al., A model of evolutionary changes in proteins, in Atlas of Protein Sequence and Structure, M. O. Dayhoff, Editor. 1978, National Biomedical Research Foundation: Washington D.C.) and Venezia (Venezia and O'Hara, Rapid motif compliance scoring with match weight sets. Comput Appl Biosci, 9(1):65–9 (1993)) protein techniques. The coefficient in these matrices will be determined experimentally for the disclosed method. Below is an example of matrices (with illustrative coefficients) representing position 1 and 2, where the columns represent the upper strand nucleotide and the rows represent the lower strand nucleotide. The actual coefficients can be determined empirically.

|   | Position 1<br>A T C G | Position 2<br>A T C G |
|---|---|---|
|   | A[.02,.90,.03,.05]<br>T[.90,.02,.03,.05]<br>C[.02,.03,.05,.90]<br>G[.03,.02,.90,.05] | A[.01,.97,.01,.01]<br>T[.97,.01,.01,.01]<br>C[.01,.01,.01,.97]<br>G[.01,.01,.97,.01] |

For the case of a perfect match detection on the hexamer ATXXXX the score is determined to be the product of the coefficients of the matrices, shown below here in bold; 0.90×0.97=0.87.

|   | Position 1<br>A T C G | Position 2<br>A T C G |
|---|---|---|
|   | A[.02,.90,.03,.05]<br>T[.90,.02,.03,.05]<br>C[.02,.03,.05,.90]<br>G[.03,.02,.90,.05] | A[.01,.97,.01,.01]<br>T[.97,.01,.01,.01]<br>C[.01,.01,.01,.97]<br>C[.01,.01,.97,.01] |

A case where a singe base mismatch in one strand occurs, for example A→G in position 1 on the hexamer side, the score is determined in a similar fashion, to be 0.05×0.97= 0.05

|   | Position 1<br>A T C G | Position 2<br>A T C G |
|---|---|---|
|   | A[.02,.90,.03,.05]<br>T[.90,.02,.03,.05]<br>C[.02,.03,.05,.90]<br>G[.03,.02,.90,.05] | A[.01,.97,.01,.01]<br>T[.97,.01,.01,.01]<br>C[.01,.01,.01,.97]<br>G[.01,.01,.97,.01] |

This procedure can be extended to an arbitrary number of bases in a similar manner. For a given number of nucleotides the score can be computed for all possible mismatches and rank ordered to reveal the most probable identity. A cut-off score can be used to reduce the number of possible identities from the matrix estimation. For example using the example matrices above, sequences with a threshold score above 0.50 would yield only one sequence, that being a sequence which matches the probe.

This method of estimating sequences and their respective probability scores from the universe of mismatch events for a said probe can from extended from 1 to n, where n is the number of free bases available for hybridization.

In an organism that has not been completely characterized (i.e. at least sequenced and consensus sequence assembled) one can compute a confidence value for uniqueness if one assumes a random distribution of bases. For example, if one has a candidate of 15 bases in length, in an organism which has an estimated $10^8$ base genome, one expects the 15 base fragment to be unique because $10^8/4^{15}=0.1$ is much less than 1. The genome would have to be 10 times larger before one would expect an occurrence of two instances of the particular 15 base fragment.

The distributions, in known genomes, are known not to be completely random and the initial assumption of a random distribution can be improved as information is gathered. This new information can be used to assign and use confidence values.

As an example, consider a fictitious gene family ABCD, whose members are ABCD1, ABCD2 and ABCD3. The three members were discovered following some event such as heat shock, and they are thus putatively assigned to belong to the heat shock family of genes and happen to have significant stretches of conserved sequence among the family of genes. Also consider the organism to be a plant, where ABCD1 was isolated from the plant root, ABCD2 was isolated from the plant leaf, and ABCD3 was isolated from the plant flower. The estimation matrix may look like

|   | 1 2 3 |
|---|---|
|   | ABCD1[.60,.15,.05]<br>ABCD2[.25,.60,.15]<br>ABCD3[.05,.15,.60] | where the column 1 represents root, column 2 represents leaf and column 3 represents flower.

In a single experiment where one has high confidence in the sequence but the sequence may belong to one of the three known members of the family, the source of the sample (i.e. root, leaf or flower) allow estimation of the identity of the gene. For the fully mathematically closed treatment the matrix must contain all elements of the family, here to allow for a still to be found gene in this family, the rows and columns do not add to 1; all the other members are assigned a sum of 0.05, the values to be updated as the amount of information known about the organism increases.

One can extend this estimation to include organism homology. That is, if one were to search a database of all organisms for a given sequence from gene ABCD1 of Plant 1 there may be matches to Plant 2, Plant 3, Mammal 1, etc. The estimation matrix would be constructed from the known organism data in the database.

The calculations and analysis described above can be illustrated using the following example of construction of a catalog. Consider a two probe array, a control sample, and a tester sample. Consider the two probes to have the known sequences: A, <substrate--linker--AGGGAG-3'>, and, B, <substrate--linker--ATGGAG>. These probes will capture their cognate sequence: AA, < . . . TCCCTC . . . >, and, BB, < . . . TACCTC . . . > from the control and tester samples, as well as some mismatched species with lower probability as described herein. Utilizing the estimation matrix technique as discussed above one calculates the probabilities of the correct matching.

The disclosed method is conducted on the control and tester, resulting signals are collected from the probe array, and a catalog is made which contains the four signals:

|   | control |     |   | tester |     |
|---|---------|-----|---|--------|-----|
|   | AA      | BB  |   | AA     | BB  |
| A | .30     | .03 | A | .80    | .10 |
| B | .03     | .50 | B | .03    | .50 |

The catalog also contains the probabilities, and/or entries derived from the probabilities, for each probe/target combination, as discussed above. For purpose of illustration, let us assume that the probability of having probe sequence A paired with target sequence AA is 0.80, and the probability of having probe sequence A paired with sequence BB is 0.10, probe sequence B paired with target sequence AA is 0.05, and the probability of having probe sequence B paired with sequence BB is 0.75, or

|   | estimation | |
|---|---|---|
|   | AA | BB |
| A | .80 | .10 |
| B | .05 | .75 |

It is a simple matter of application of linear algebra to determine the signals corresponding to each target. Here, for example, multiplying the corresponding entries together to convert the control and tester to the pattern corresponding to the probabilistic pattern of the target of interest. For example, the total signal ascribed, in the control sample, to AA target is 0.30×0.80 (on A probe site, perfect match)+ 0.03×0.05 (on B probe site, imperfect match)= approximately 0.24. On the tester sample, the AA target signal is 0.80×0.80+0.03×0.05 =approximately 0.64. Comparison of the pattern for the control and tester, for the sequence corresponding to AA, exhibits an increase in the relative amount of AA from 0.24 to 0.64 for control to tester respectively. All other entries in the pattern are calculated in the same fashion.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of ordinary skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of identifying nucleic acid fragments in nucleic acid samples, the method comprising
   (a) mixing one or more nucleic acid samples with one or more different hairpin primers, wherein each hairpin primer comprises a different primer sequence,
   (b) incubating the samples under conditions that promote amplification of nucleic acids in the samples, wherein amplified nucleic acid fragments are formed which have hairpin primer sequences at one or both ends,
   (c) incubating the samples under conditions that promote formation of hairpin structures by the hairpin primer sequences at the ends of the amplified fragments,
   (d) hybridizing each sample with a plurality of detector probes and covalently coupling the hairpin structures to the probes, wherein each probe has a different sequence, and
   (e) detecting, directly or indirectly, coupling of the amplified fragments to the detector probes.

2. The method of claim 1 wherein the probes are all of the same length.

3. The method of claim 2 wherein the detector probes are six, seven, or eight nucleotides long.

4. The method of claim 1 wherein the probes all have similar hybrid stability.

5. The method of claim 1 wherein the amplified fragments are covalently coupled to the detector probes by ligation.

6. The method of claim 1 further comprising, prior to step (a), dividing the sample into a plurality of index samples, wherein a different hairpin primer is mixed with each index sample, wherein steps (a) through (e) are performed with each index sample.

7. The method of claim 6 further comprising, prior to step (b),
   dividing each index sample into a set of two or more of secondary index samples, and
   mixing each secondary index sample in each set of secondary index samples with a different set of one or more second primers.

8. The method of claim 6 further comprising,
   prior to step (a), dividing each index sample into a set of two or more of secondary index samples,
   prior to, simultaneous with, or following step (a), mixing each secondary index sample in each set of secondary index samples with a different set of one or more second primers,
   wherein mixing each index sample with one or more different hairpin primers is accomplished by mixing the one or more different hairpin primers with each secondary index sample in a set of secondary index samples.

9. The method of claim 1 further comprising, following step (b), separating the strands of the amplified fragments and proceeding with step (c) using only one of the strands.

10. The method of claim 9 wherein the strands are separated using a capture tag incorporated into one of the strands.

11. The method of claim 10 wherein the capture tag is incorporated into the hairpin primers.

12. The method of claim 9 wherein the strands are separated by selective digestion of one of the strands.

13. The method of claim 12 wherein the linkages between a plurality of nucleotides at the 5' end of each hairpin primer are insensitive to nuclease digestion.

14. The method of claim 13 wherein the linkages between a plurality of nucleotides at the 5' end of each hairpin primer are phosphorothioate linkages.

15. The method of claim 1 wherein the concentration of the various nucleic acid fragments in the samples are normalized.

16. The method of claim 15 wherein the strands of the nucleic acid fragments are separated and the concentration of the nucleic acid fragments is normalized by immobilizing one strand of the nucleic acid fragments, denaturing the nucleic acid fragments, renaturing the nucleic acid fragments for a time greater than the $c_0t_{1/2}$ for abundant nucleic acid fragments and less than the $c_0t_{1/2}$ for rare nucleic acid fragments, and collecting the un-renatured nucleic acid fragments.

17. The method of claim 1 further comprising, prior to step (e), amplifying the amplified fragments coupled to the detector probes.

18. The method of claim 1 wherein each detector probe is immobilized on a substrate.

19. The method of claim 18 wherein all of the detector probes are immobilized on the same substrate.

20. The method of claim 18 wherein all of the detector probes are immobilized on a different substrate.

21. The method of claim 20 wherein the substrates are beads.

22. The method of claim 18 wherein the detector probes are immobilized on a plurality of different substrates such that at least one detector probe is immobilized on one substrate and at least one other detector probe, respectively, is immobilized on a different substrate.

23. The method of claim 18 wherein the detector probes are in an array.

24. The method of claim 1 wherein each detector probe is associated with a capture tag, sorting tag, or both.

25. The method of claim 24 wherein the detector probes are captured via the capture tags.

26. The method of claim 24 wherein the detector probes are sorted via the sorting tags.

27. The method of claim 24 wherein the detector probes are associated with a plurality of different capture tags or a plurality of different sorting tags.

28. The method of claim 1 wherein the detector probes are in an array, wherein each detector probe is immobilized at a different location in the array, and wherein detecting coupling of amplified fragments to detector probes is accomplished by detecting the presence of amplified fragments at different locations in the arrays.

29. The method of claim 28 wherein the location, amount, or location and amount of amplified fragments in the arrays constitutes a pattern of amplified fragments in the arrays, the method further comprising comparing the pattern of amplified fragments in the arrays with the pattern of amplified fragments in arrays determined in a separate procedure using a second nucleic acid sample.

30. The method of claim 29 further comprising comparing the pattern of amplified fragments in the arrays with the pattern of amplified fragments in arrays determined in a plurality of separate procedures using a plurality of different nucleic acid samples.

31. The method of claim 1 further comprising, following covalent coupling in step (d), incubating the samples with T4 endonuclease VII.

32. The method of claim 1 wherein the nucleic acid fragments are amplified by PCR.

33. The method of claim 1 wherein each hairpin primer contains a label, wherein coupling of the amplified fragments to the probes is detected via the label.

34. The method of claim 33 wherein the label is detectable by nuclear magnetic resonance, electron paramagnetic resonance, surface enhanced raman scattering, surface plasmon resonance, fluorescence, phosphorescence, chemiluminescence, resonance raman, microwave, or a combination thereof.

35. The method of claim 1 wherein the presence of the amplified fragments is detected by rolling circle replication of an amplification target circle wherein replication is primed by primer sequences at the end of the amplified fragments.

36. The method of claim 1 wherein the pattern of the amount of amplified fragments coupled to different detector probes constitutes a catalog of nucleic acid fragments in the nucleic acid sample, wherein the pattern is compared to a predicted pattern based on probabilities of base mismatches of sequences hybridized to the detector probes.

37. The method of claim 1 wherein detecting coupling of the amplified fragments to the detector probes is accomplished by detecting mass labels associated with the coupled fragments, mass labels associated with the detector probes, or a combination thereof, by mass spectroscopy.

38. The method of claim 37 wherein the mass labels associated with the coupled fragments and mass labels associated with the detector probes are detected by matrix-assisted laser desorption/ionization time-of-flight mass spectroscopy.

39. The method of claim 37 wherein the composition of the mass labels associated with the coupled fragments and mass labels associated with the detector probes are determined by analyzing the fragmentation pattern.

40. The method of claim 37 wherein uncoupled fragments are washed away from the detector probes prior to detection of the coupled fragments.

41. The method of claim 37 wherein the hairpin primers, the detector probes, or both, contain a photocleavable nucleotide, wherein the method further comprises, following coupling of the amplified fragments to the detector probes, photocleavage of the photocleavable nucleotides, and detection of one or both strands of the coupled amplified fragment by mass spectroscopy.

42. The method of claim 37 further comprising, following coupling of the amplified fragments to the detector probes, incubation of the couple fragments and detector probes with one or more nucleic acid cleaving reagents, and detection of one or both strands of the coupled fragment by mass spectroscopy.

43. The method of claim 1 further comprising performing steps (a) through (c) on one or more control nucleic acid samples, wherein the hairpin primers used with the control nucleic acid samples contain a different label from the label of the hairpin primers used with the nucleic acid samples, mixing the control nucleic acid samples with corresponding nucleic acid samples and proceeding with step (d) by hybridizing the mixed samples with the detector probes, detecting coupling of both types of amplified fragments to different detector probes, and identifying differences in the pattern of coupling of amplified fragments to probes from the nucleic acid samples and the control nucleic acid samples.

44. The method of claim 1 further comprising performing steps (a) through (c) on one or more control nucleic acid samples, wherein the hairpin primers used with the nucleic acid samples contain a labile nucleotide in the loop, mixing the control nucleic acid samples with corresponding nucleic acid samples and proceeding with step (d) by hybridizing the mixed samples with the detector probes, detecting coupling of amplified fragments from both types of samples to different detector probes, treating the mixed nucleic acid samples to cleave the labile nucleotide, detecting coupling of amplified fragments from nucleic acid samples to different detector probes, and identifying differences in the pattern of coupling of amplified fragments to probes from the nucleic acid samples and the control nucleic acid samples.

45. The method of claim 1 wherein the detector probes are in an array, wherein each probe is immobilized at a different location in the array, wherein the location of amplified fragments in the array constitutes a pattern of coupling of amplified fragments to probes in the array, the method further comprising comparing the pattern of coupling of amplified fragments in the arrays with the pattern of amplified fragments in arrays determined in a separate procedure using a second nucleic acid sample.

46. The method of claim 1 wherein the pattern of the presence, amount, presence and amount, or absence of amplified fragments coupled to different detector probes constitutes a catalog of nucleic acid fragments in the nucleic acid sample.

47. The method of claim 46 further comprising preparing a second catalog of nucleic acid fragments in a second nucleic acid sample and comparing the first catalog and second catalog.

48. The method of claim 47 further comprising identifying or preparing nucleic acid fragments corresponding the nucleic acid fragments present at a threshold amount in the first nucleic acid sample but not present at the threshold amount in the second nucleic acid sample.

49. The method of claim 47 wherein the second nucleic acid sample is a sample from the same type of organism as the first nucleic acid sample.

50. The method of claim 47 wherein the second nucleic acid sample is a sample from the same type of tissue as the first nucleic acid sample.

51. The method of claim 47 wherein the second nucleic acid sample is a sample from the same organism as the first nucleic acid sample.

52. The method of claim 51 wherein the second nucleic acid sample is obtained at a different time than the first nucleic acid sample.

53. The method of claim 47 wherein the second nucleic acid sample is a sample from a different organism than the first nucleic acid sample.

54. The method of claim 47 wherein the second nucleic acid sample is a sample from a different type of tissue than the first nucleic acid sample.

55. The method of claim 47 wherein the second nucleic acid sample is a sample from a different species of organism than the first nucleic acid sample.

56. The method of claim 47 wherein the second nucleic acid sample is a sample from a different strain of organism than the first nucleic acid sample.

57. The method of claim 47 wherein the second nucleic acid sample is a sample from a different cellular compartment than the first nucleic acid sample.

58. The method of claim 47 further comprising identifying or preparing nucleic acid fragments corresponding the nucleic acid fragments present in the first nucleic acid sample but not present in the second nucleic acid sample.

59. The method of claim 58 further comprising using the nucleic acid fragments as probes.

60. The method of claim 59 wherein using the nucleic acid fragments as probes is accomplished by repeating steps (a) through (d) with a different nucleic acid sample, wherein the nucleic acid fragments are used as detector probes in steps (d) and (e).

61. The method of claim 1 further comprising determining the sequence of a portion of at least one of the amplified fragments.

62. The method of claim 61 wherein the portion of the amplified fragment corresponds to the sequence complementary to the primer sequence of the hairpin primer and the sequence adjacent to the sequence complementary to the primer sequence to which the detector probe hybridized.

63. The method of claim 62 further comprising detecting or amplifying a nucleic acid corresponding to a nucleic acid fragment in the nucleic acid sample using a probe or primer based on the determined sequence of the portion of the nucleic acid fragment.

64. The method of claim 1 wherein each hairpin primer or detector probe contains a label, wherein coupling of the amplified fragments to the detector probes is detected via the label.

65. The method of claim 64 wherein each hairpin primer contains a label,
wherein detecting coupling of the amplified fragments to the detector probes is accomplished by
separating coupled fragments from uncoupled fragments, and
detecting the labels of the coupled fragments.

66. The method of claim 65 wherein each different hairpin primer contains a different label, wherein each detector probe is associated with a capture tag or a sorting tag, wherein separating coupled fragments from uncoupled fragments is accomplished by separating the detector probes from the uncoupled fragments using the capture tags or sorting tags, wherein the coupled fragments separate with the detector probes.

67. The method of claim 66 wherein the sorting tag is a fluorescent label, and wherein separating the detector probes from the uncoupled fragments is accomplished using a fluorescent label sorter.

68. The method of claim 64 wherein each detector probe contains a label,
wherein detecting coupling of the amplified fragments to the detector probes is accomplished by
separating coupled detector probes from uncoupled detector probes, and
detecting the labels of the detector probes.

69. The method of claim 68 wherein each different detector probe contains a different label, wherein each amplified fragment is associated with a capture tag or a sorting tag, wherein separating coupled detector probes from uncoupled detector probes is accomplished by separating the amplified fragments from the uncoupled detector probes using the capture tags or sorting tags, wherein the coupled detector probes separate with the amplified fragments.

70. The method of claim 69 wherein the sorting tag is a fluorescent label, and wherein separating the amplified fragments from the uncoupled detector probes is accomplished using a fluorescent label sorter.

71. The method of claim 64 wherein the labels are fluorescent, phosphorescent, or chemiluminescent labels.

72. The method of claim 71 wherein at least two of the labels are distinguished temporally via different fluorescent, phosphorescent, or chemiluminescent emission lifetimes.

73. The method of claim 64 wherein the labels are detectable by nuclear magnetic resonance, electron paramagnetic resonance, surface enhanced raman scattering, surface plasmon resonance, fluorescence, phosphorescence, chemiluminescence, resonance raman, microwave, or a combination thereof.

74. The method of claim 73 wherein the label is detected using nuclear magnetic resonance, electron paramagnetic resonance, surface enhanced raman scattering, surface plasmon resonance, fluorescence, phosphorescence, chemiluminescence, resonance raman, microwave, or a combination thereof.

75. The method of claim 64 wherein the labels are beads comprising a label.

76. The method of claim 75 wherein the label is a molecular barcode.

77. The method of claim 64 wherein the labels are mass labels.

78. The method of claim 1 further comprising
performing steps (a) through (e) on a control nucleic acid sample,
identifying differences between the nucleic acid sample and the control nucleic acid sample in the pattern of amplified fragments coupled to different detector probes.

79. The method of claim 78 wherein the hairpin primers used with the control nucleic acid sample contain a different label from the label of the hairpin primers used with the nucleic acid sample,
wherein the control nucleic acid samples are mixed with corresponding nucleic acid samples prior to step (d).

80. The method of claim 1 further comprising
performing steps (a) through (e) on a plurality of nucleic acid samples.

81. The method of claim 80 further comprising
performing steps (a) through (e) on a control nucleic acid sample,
identifying differences between the nucleic acid samples and the control nucleic acid sample in the pattern of amplified fragments coupled to different detector probes.

82. The method of claim 80 further comprising
identifying differences between the nucleic acid samples in the pattern of amplified fragments coupled to different detector probes.

83. A method of identifying a nucleic acid sequence in a nucleic acid sample, the method comprising
- (a) mixing a nucleic acid sample with a hairpin primer and a second primer, wherein the hairpin primer and the second primer comprise primer sequences complementary to sequences flanking and on opposite strands of a nucleic acid sequence of interest,
- (b) incubating the nucleic acid sample under conditions that promote amplification of the nucleic acid sequence of interest, wherein a nucleic acid fragment is formed which comprises the nucleic acid sequence of interest flanked by sequences of the hairpin primer and the second primer,
- (c) incubating the nucleic acid sample under conditions that promote formation of a hairpin structure by the sequence of the hairpin primer,
- (d) hybridizing the nucleic acid sample with a plurality of detector probes and coupling the hairpin structure to a probe, wherein each probe has a different sequence, and
- (e) detecting, directly or indirectly, coupling of the nucleic acid fragment to a detector probe.

84. A method of identifying nucleic acid fragments in a nucleic acid sample, the method comprising
- (a) dividing the sample into a plurality of index samples, wherein the index samples are organized into sets of index samples wherein each set comprises a plurality of index samples,
- (b) mixing each index sample in a set of index samples with one or more different hairpin primers, wherein each hairpin primer comprises a different primer sequence, and mixing each index sample with one or more different second primers,
- (c) incubating the index samples under conditions that promote amplification of nucleic acids in the samples, wherein amplified nucleic acid fragments are formed which are flanked by hairpin primer sequences and second primer sequences,
- (d) incubating the index samples under conditions that promote formation of hairpin structures by the hairpin primer sequences at the ends of the amplified fragments,
- (e) hybridizing each index sample with a plurality of detector probes and coupling the hairpin structures to the probes, wherein in a given set of detector probes each probe has a different sequence, and
- (f) detecting, directly or indirectly, coupling of the amplified fragments to different detector probes.

85. A method of comparing nucleic acid samples, the method comprising
- (a) comparing a catalog of nucleic acid fragments in a first nucleic acid sample with a catalog of nucleic acid fragments in a second nucleic acid sample, and
- (b) identifying or preparing nucleic acid fragments corresponding to the nucleic acid fragments present in the first nucleic acid sample but not present in the second nucleic acid sample;
- wherein the catalogs of nucleic acid fragments are each produced by
  - (i) mixing the nucleic acid sample with one or more different hairpin primers, wherein each hairpin primer comprises a different primer sequence,
  - (ii) incubating the sample under conditions that promote amplification of nucleic acids in the sample, wherein amplified nucleic acid fragments are formed which have hairpin primer sequences at one or both ends,
  - (iii) incubating the sample under conditions that promote formation of hairpin structures by the hairpin primer sequences at the ends of the amplified fragments,
  - (iv) hybridizing the sample with a plurality of detector probes and covalently coupling the hairpin structures to the probes, wherein each probe has a different sequence, and
  - (v) detecting, directly or indirectly, coupling of the amplified fragments to the detector probes,
  - wherein the pattern of the presence, amount, presence and amount, or absence of amplified fragments coupled to different detector probes constitutes the catalog of nucleic acid fragments in the nucleic acid sample.

86. The method of claim 85 wherein nucleic acid fragments present in the first nucleic acid sample but not present in the second nucleic acid sample are nucleic acid fragments present at a threshold amount in the first nucleic acid sample but not present at the threshold amount in the second nucleic acid sample.

87. The method of claim 85 wherein the pattern of the presence, amount, presence and amount, or absence of amplified fragments coupled to different detector probes is embodied by the sequences represented by the coupled amplified fragments.

88. The method of claim 87 wherein each represented sequence corresponds to sequence complementary to the primer sequence of the hairpin primer and sequence adjacent to the sequence complementary to the primer sequence to which the detector probe hybridized.

89. The method of claim 85 wherein the probes are all of the same length.

90. The method of claim 85 wherein the probes all have similar hybrid stability.

91. A method of identifying nucleic acid fragments in a nucleic acid sample, the method comprising
- (a) incubating a nucleic acid sample with one or more nucleic acid cleaving reagents that collectively generate sticky ends having a plurality of different sequences to produce nucleic acid fragments with sticky ends,
- (b) dividing the sample into a plurality of index samples,
- (c) mixing a different adaptor-indexer with each index sample and covalently coupling the adaptor-indexers to the nucleic acid fragments, wherein each adaptor-indexer has a different sticky end, wherein each sticky end of the adaptor-indexes is compatible with a sticky end generated by the nucleic acid cleaving reagents, wherein each index sample has a different adaptor-indexer,
- (d) mixing each index sample with one or more different hairpin primers, wherein each hairpin primer comprises a different primer sequence, wherein each primer sequence is complementary to all or part of the sequence of at least one of the adaptor-indexers,
- (e) incubating the index samples under conditions that promote amplification of nucleic acids in the samples, wherein amplified nucleic acid fragments are formed which have hairpin primer sequences at one or both ends, (f) incubating the index samples under conditions that promote formation of hairpin structures by the hairpin primer sequences at the ends of the amplified fragments, (g) hybridizing each index sample with a plurality of detector probes and covalently coupling the hairpin structures to the probes, wherein each probe has a different sequence, and (h) detecting coupling of the amplified fragments to different detector probes.

92. The method of claim 91 further comprising determining the sequence of a portion of at least one of the amplified fragments.

93. The method of claim 92 wherein the portion of the nucleic acid fragments corresponds to the sticky end sequence, the sequence adjacent to the sticky end sequence to which the detector probe hybridized, and the recognition sequence of the nucleic acid cleaving reagent.

94. The method of claim 93 wherein the portion includes a gap of known length but unknown sequence between the sequence adjacent to the sticky end and the recognition sequence of the nucleic acid cleaving reagent.

95. The method of claim 94 wherein the portion has the structure

A-B-C-D wherein A is the recognition sequence of the nucleic acid cleaving reagent, B is the gap of unknown sequence, C is the sequence to which the detector probe hybridized, and D is the sticky end sequence.

96. The method of claim 91 wherein, for at least one of the hairpin primer sequences, the sticky end sequence is involved in the stem of the hairpin structure but none of the fragment sequence adjacent to the sticky end sequence is involved in the stem of the hairpin structure.

97. The method of claim 91 wherein the probes are all of the same length.

98. The method of claim 91 wherein the probes all have similar hybrid stability.

99. The method of claim 91 further comprising, prior to step (c), incubating the index samples with one or more second nucleic acid cleaving reagents, and mixing a second adaptor with each digested index sample and covalently coupling the second adaptor to the nucleic acid fragments, wherein the second adaptor has an end compatible with the end generated by one of the second nucleic acid cleaving reagents.

100. The method of claim 99 further comprising, prior to digestion with the second nucleic acid cleaving reagents, dividing each index sample into a set of two or more secondary index samples, wherein each secondary index sample in each set of secondary index samples is digested with a different set of one or more second nucleic acid cleaving reagents.

101. The method of 99 further comprising, simultaneous with step (d)

mixing each secondary index sample in each set of secondary index samples with a different set of one or more second primers, wherein each secondary primer is complementary to all or part of the sequence of at least one of the second adaptors.

102. The method of claim 91 further comprising, following step (e), separating the strands of the amplified fragments and proceeding with step (d) using only one of the strands.

103. The method of claim 91 further comprising, following covalent coupling in step (e), incubating the index samples with T4 endonuclease VII.

104. The method of claim 91 wherein each hairpin primer contains a label, wherein the presence of the amplified fragments is detected via the label.

105. The method of claim 91 further comprising performing steps (a) through (f) on a control nucleic acid sample to produce control index samples, wherein the hairpin primers used with the control nucleic acid sample contain a different label from the label of the hairpin primers used with the nucleic acid sample, mixing the control index samples with corresponding index samples and proceeding with step (g) by hybridizing the mixed samples with the detector probes, identifying differences between the nucleic acid sample and the control nucleic acid sample in the pattern of amplified fragments coupled to different detector probes.

106. A kit comprising a set of hairpin primers wherein each hairpin primer has a different primer sequence, and a plurality of detector probes, wherein each probe has a different sequence, wherein the detector probes are nucleic acid fragments prepared by (a) mixing one or more nucleic acid samples with one or more different hairpin primers, wherein each hairpin primer comprises a different primer sequence, (b) incubating the samples under conditions that promote amplification of nucleic acids in the samples, wherein amplified nucleic acid fragments are formed which have hairpin primer sequences at one or both ends, (c) incubating the samples under conditions that promote formation of hairpin structures by the hairpin primer sequences at the ends of the amplified fragments, (d) hybridizing each sample with a plurality of detector probes and covalently coupling the hairpin structures to the probes, wherein each probe has a different sequence, and (e) detecting, directly or indirectly, coupling of the amplified fragments to the detector probes, wherein the pattern of amplified fragments coupled to different detector probes constitutes a catalog of nucleic acid fragments in the nucleic acid sample, (f) preparing a second catalog of nucleic acid fragments in a second nucleic acid sample and comparing the first catalog and second catalog, and (g) preparing nucleic acid fragments corresponding the nucleic acid fragments present in the first nucleic acid sample but not present in the second nucleic acid sample.

* * * * *